United States Patent [19]
Wu et al.

[11] Patent Number: 6,080,888
[45] Date of Patent: Jun. 27, 2000

[54] PREPARATION OF OLEFINIC COMPOUNDS AND CARBOXYLIC DERIVATIVES THEREOF

[75] Inventors: Tse-Chong Wu; Kannappan C. Chockalingham; W. Dirk Klobucar; Gary D. Focht, all of Baton Rouge, La.

[73] Assignee: Albemarle Corporation, Richmond, Va.

[21] Appl. No.: 08/780,310

[22] Filed: Jan. 8, 1997

[51] Int. Cl.$^7$ .................................................. C07C 63/34
[52] U.S. Cl. .................... 562/467; 562/406; 568/632; 585/26; 585/436; 260/665 R; 260/665 G
[58] Field of Search .................... 585/26, 436; 562/406, 562/467; 568/632; 260/665 R, 665 G

[56] References Cited

U.S. PATENT DOCUMENTS

| | | | |
|---|---|---|---|
| 3,159,649 | 12/1964 | Brown et al. | 260/343.3 |
| 3,228,831 | 1/1966 | Nicholson et al. | 167/53 |
| 3,385,886 | 5/1968 | Nicholson et al. | 260/515 |
| 3,562,336 | 2/1971 | Nelson | 260/613 |
| 3,600,437 | 8/1971 | Marshall | 260/520 |
| 3,626,012 | 12/1971 | Fried et al. | 260/599 |
| 3,637,767 | 1/1972 | Alvarez | 260/348 R |
| 3,641,127 | 2/1972 | Farge et al. | 260/516 |
| 3,651,106 | 3/1972 | Harrison | 260/429 R |
| 3,651,148 | 3/1972 | Nelson | 260/606.5 B |
| 3,651,149 | 3/1972 | Harrison | 260/606.5 B |
| 3,652,683 | 3/1972 | Harrison | 260/612 D |
| 3,658,858 | 4/1972 | Harrison | 260/429 R |
| 3,658,863 | 4/1972 | Harrison | 260/438.1 |
| 3,663,584 | 5/1972 | Alvarez | 260/429.9 |
| 3,663,713 | 5/1972 | Fried et al. | 424/333 |
| 3,681,432 | 8/1972 | Nelson | 260/473 F |
| 3,683,015 | 8/1972 | Dyson | 260/520 |
| 3,686,183 | 8/1972 | Dyson | 260/284 |
| 3,694,476 | 9/1972 | Alvarez | 260/429 R |
| 3,720,708 | 3/1973 | Halpern | 260/519 |
| 3,755,427 | 8/1973 | Adams et al. | 260/515 A |
| 3,758,544 | 9/1973 | Alvarez | 260/465 F |
| 3,787,580 | 1/1974 | Fried et al. | 424/308 |
| 3,821,253 | 6/1974 | Fried et al. | 260/340.9 |
| 3,828,033 | 8/1974 | Nelson | 260/240 R |
| 3,873,594 | 3/1975 | Alvarez | 260/465 F |
| 3,896,157 | 7/1975 | Fried et al. | 260/469 |
| 3,904,682 | 9/1975 | Fried et al. | 260/520 |
| 3,904,683 | 9/1975 | Day et al. | 260/520 |
| 3,906,038 | 9/1975 | Fried et al. | 260/507 R |

(List continued on next page.)

FOREIGN PATENT DOCUMENTS

| | | |
|---|---|---|
| 59-10545 | 1/1984 | Japan . |
| 380563 | 9/1932 | United Kingdom . |

OTHER PUBLICATIONS

DeVries et al; "Synthesis of High–Purity o–and p–Vinyltoluenes by the Heck Palladium–Catalyzed Arylation Reaction"; Organometallics (1994) vol. 13, pp. 2405–2411.

Heck; "Palladium Reagents in Organic Syntheses"; Academic Press (1985), pp. 276–291.

Patel, et al; "Palladium–Catalyzed Vinylation of Conjugated Dienes"; J. Org. Chem. (1979) vol. 44, pp. 918–921

Lewis; "Methylation of Phenol by Dimethyl Sulfate"; Industrial and Engineering Chemistry (1930), vol. 22, pp. 397–398.

Ohta et al; "Asymmetric Hydrogenation of Unsaturated Carboxylic Acids Catalyzed by BINAP–Ruthenium(II) Complexes"; J. Org. Chem. (1987), vol. 52, pp. 3174–3176.

Pinder; "The Hydrogenolysis of Organic Halides"; Synthesis, (1980), pp. 425–452.

Rajagopal et al; "Mechanism of Palladium–Catalyzed Transfer Hydrogenolysis of Aryl Chlorides by Formate Salts"; J. Or. Chem. (1995), vol. 60, pp. 1347–1355.

Alper et al; "The Regiospecific Palladium Catalysed Hydrocarboxylation of Alkenes under Mild Conditions"; J. Chem. Sol. Chem. Commun. (1983), pp. 1270–1271.

Horeau et al; "Steroids depourvus de noyau C (III). Sur une lactone correspondant a un isomere de la bis–dehydrocestrolactone"; Memoires Presents A La Societe Chimique (1959), pp. 1854–1857.

Heitz et al; "Synthesis of monomers and polymers by the Heck reaction"; Makromoi Chem. (1988) vol. 1989, pp. 119–127.

Marques et al; "Facile Hydrodehalogenation with $H_2$ and Pd/C Catalyst under Multiphase Conditions. 2. Selectivity and Kinetics"; J. Org. Chem. (1994) vol. 59, pp. 3830–3837.

Marques et al; Facile Hydrodehalogenation with $H_2$ and Pd/C Catalyst under Multiphase Conditions. 3. Selective Removal of Halogen from Functionalized Aryl Ketones. 4. Aryl Halide–Promoted Reduction of Benzyl Alcohols to Alkanes; J. Org. Chem. (1995), vol. 60, pp. 2430–2435.

Piccolo et al; "Zinc Salt Catalyzed Rearrangement of Acetals of Optically Active Aryl 1–Chloroethyl Ketones; Synthesis of Optically Active 2–Arylpropionic Acids and Ester[1]"; J. Org. Chem. (1987), vol. 52, pp. 10–14.

Stinson; "Technological Innovation Thrives in Fine Chemicals Industry"; Science/Technolgy; (1996), pp. 35–61.

Horeau, et al; No. 287. "Steroids devoid of C nucleus (iii). On a lactone corresponding to an isomer of bis–dehydroestrolactone"; Soc. Chim., 5th Series, '59—Reports, pp. 1854–1857.

Marques, et al; "Facile Hydrodehalogenation with Hydrogen and Pd/C Catalyst under Multiphase Conditions"; J. Org. Chem. '93, vol. 58, No. 19, pp. 5256–5260.

*Primary Examiner*—Paul F. Shaver
*Attorney, Agent, or Firm*—Philip M. Pippenger

[57] ABSTRACT

Arylolefinic compounds are prepared by reacting aryl halide with an olefinic compound in the presence of a polar liquid reaction medium containing (a) secondary or tertiary amine as a hydrogen halide acceptor (b) a catalyst system formed from (i) Pd or Pd(0) compound, and/or Pd(I) salt or Pd(II) salt, and (ii) a tertiary phosphine ligand, and (c) a reaction accelerating amount of water in the range of about 0.5 to about 5 weight percent of the total weight of the reaction mixture. The arylolefinic compounds can be converted to an arylcarboxylic acid by hydrocarboxylation with CO in a reaction medium freed of amine and containing water and a Pd catalyst system as above in which a copper component may be included, and which preferably includes an ether such as THF.

56 Claims, No Drawings

U.S. PATENT DOCUMENTS

| | | | |
|---|---|---|---|
| 3,914,293 | 10/1975 | Fried et al. | 260/512 C |
| 3,923,900 | 12/1975 | Petracek | 260/590 |
| 3,935,273 | 1/1976 | Fried et al. | 260/600 R |
| 3,958,012 | 5/1976 | Fried et al. | 424/333 |
| 3,959,364 | 5/1976 | Armitage et al. | 260/515 R |
| 3,960,936 | 6/1976 | Fried et al. | 260/488 CD |
| 3,960,957 | 6/1976 | Alvarez | 260/566 A |
| 3,975,432 | 8/1976 | Alvarez | 260/520 R |
| 3,978,116 | 8/1976 | Fried et al. | 260/500.5 H |
| 3,978,124 | 8/1976 | Fried et al. | 260/558 R |
| 3,980,699 | 9/1976 | Fried et al. | 260/515 R |
| 3,988,365 | 10/1976 | Gallegra | 260/520 D |
| 3,994,968 | 11/1976 | Alvarez | 260/520 D |
| 3,998,966 | 12/1976 | Fried et al. | 424/308 |
| 4,001,301 | 1/1977 | Fried et al. | 260/473 F |
| 4,005,093 | 1/1977 | Zenitz | 260/293.62 |
| 4,009,197 | 2/1977 | Fried et al. | 260/473 F |
| 4,028,366 | 6/1977 | Zenitz | 260/293.62 |
| 4,045,485 | 8/1977 | Fried et al. | 260/566 A |
| 4,107,439 | 8/1978 | Walker et al. | 560/55 |
| 4,135,051 | 1/1979 | Walker | 560/105 |
| 4,142,054 | 2/1979 | Amin et al. | 560/105 |
| 4,144,397 | 3/1979 | Matthews et al. | 562/466 |
| 4,233,316 | 11/1980 | Gardocki | 424/317 |
| 4,239,914 | 12/1980 | Campolmi et al. | 562/466 |
| 4,246,164 | 1/1981 | Felder et al. | 260/501.17 |
| 4,246,193 | 1/1981 | Holton | 260/501.17 |
| 4,379,148 | 4/1983 | Sato et al. | 424/232 |
| 4,395,571 | 7/1983 | Dvorak | 562/466 |
| 4,545,992 | 10/1985 | Kamishita | 514/161 |
| 4,560,777 | 12/1985 | Giordano et al. | 549/374 |
| 4,571,333 | 2/1986 | Hsiao et al. | 424/22 |
| 4,605,758 | 8/1986 | Schloemer | 562/418 |
| 4,609,766 | 9/1986 | Giordano et al. | 568/592 |
| 4,621,152 | 11/1986 | Bernini | 562/401 |
| 4,623,736 | 11/1986 | Walker et al. | 549/369 |
| 4,628,123 | 12/1986 | Borsotti | 568/634 |
| 4,654,438 | 3/1987 | Schloemer | 562/496 |
| 4,665,224 | 5/1987 | Corvi Mora | 560/56 |
| 4,697,036 | 9/1987 | Giordano et al. | 562/418 |
| 4,723,033 | 2/1988 | Erickson | 560/56 |
| 4,734,507 | 3/1988 | Giordano et al. | 549/450 |
| 4,736,061 | 4/1988 | Piccolo et al. | 562/466 |
| 4,749,804 | 6/1988 | Schloemer | 558/51 |
| 4,766,225 | 8/1988 | Sayo et al. | 556/16 |
| 4,803,079 | 2/1989 | Hsiao et al. | 424/468 |
| 4,810,819 | 3/1989 | Giordano et al. | 562/56 |
| 4,857,462 | 8/1989 | Maier et al. | 435/197 |
| 4,864,063 | 9/1989 | Piccolo et al. | 568/328 |
| 4,919,803 | 4/1990 | Doyle et al. | 210/198.2 |
| 4,962,230 | 10/1990 | Takaya et al. | 562/433 |
| 5,034,416 | 7/1991 | Smith | 514/568 |
| 5,081,251 | 1/1992 | Bender et al. | 546/350 |
| 5,130,603 | 7/1992 | Tokailin et al. | 313/504 |
| 5,136,069 | 8/1992 | DeVries et al. | 556/453 |
| 5,243,068 | 9/1993 | DeVries et al. | 560/205 |
| 5,243,088 | 9/1993 | Jacquot et al. | 568/656 |
| 5,256,829 | 10/1993 | Jacquot | 568/737 |
| 5,315,026 | 5/1994 | Wu | 560/105 |
| 5,426,243 | 6/1995 | Lecouve | 568/737 |
| 5,536,870 | 7/1996 | Wu | 560/56 |

PREPARATION OF OLEFINIC COMPOUNDS AND CARBOXYLIC DERIVATIVES THEREOF

TECHNICAL FIELD

This invention relates to the synthesis of certain substituted olefinic compounds, and also to subsequent conversion of such compounds to carboxylic acids, or derivatives thereof, such as salts or esters.

BACKGROUND

The palladium-catalyzed vinylation of organic halides provides a very convenient method for forming carbon-carbon bonds at unsubstituted vinylic positions. The reaction, reported by Heck (*Palladium Reagents in Organic Synthesis,* Academic Press, Canada 1985) can be used to prepare fine organics, pharmaceuticals, and specialty monomers. For example, the reaction allows a one-step synthesis of substituted styrenes from aryl bromides and is an excellent method for preparation of a wide variety of styrene derivatives. Heitz et al., *Makromol Chem.,* 189, 119 (1968).

Vinyl toluenes have been reported as the product of a homogeneous palladium-catalyzed coupling of ethylene with bromotoluenes. The reaction is performed in a two-phase solvent system composed of N,N-dimethyl formamide and water. R. A. DeVries et al., *Organometallics,* 13, 2405 (1994).

U.S. Pat. Nos. 5,136,069 and 5,243,068 to R. A. DeVries et al. describe preparation of vinylically-unsaturated compounds by reaction of a halogenated organic compound with a hydrolytically-stable, vinylically-unsaturated precursor compound in the presence of (a) a homogeneous zerovalent palladium catalyst complex, (b) an inorganic hydrogen halide acceptor and (c) a diluent which is either water or an aqueous solution containing up to 95% by volume of organic solvent.

Arylation of propylene, ethylene, styrene, and methyl acrylate with iodobenzene was found to be catalyzed by metallic palladium in methanol to give methylstyrene, styrene, t-stilbene, and methyl cinnamate, respectively. Their yields and selectivities increased significantly by the addition of excess potassium acetate as an acceptor of hydriodic acid formed. Mori et al., *Bull. Chem. Soc., Japan,* 46, 1505 (1973).

A variety of styrene derivatives and 3-vinylpyridine were prepared in moderate to good yields by the palladium-tri-o-tolylphosphine catalyzed reaction of ethylene with aryl bromides or 3-bromopyridine, respectively. (Plevyak et al., *J. Org. Chem.,* 43, 2454 (1970).

Alper et al. in *J. Chem Soc. Chem. Comm.,* 1983, 1270–1271, discloses that alkenes can react with carbon monoxide, water, hydrochloric acid and a mixture of palladium and copper to produce the hydrocarboxylated branched chain carboxylic acid. Oxygen is necessary to succeed in the reaction.

A process for preparing the branched chain carboxylic acid ibuprofen is described in Japanese Patent Application (Kokai) No. 59-10545 (Mitsubishi Petrochemical, published January, 1984), which teaches that ibuprofen can be prepared by reacting p-isobutylstyrene with carbon monoxide and water or an alcohol in the presence of a palladium(II) catalyst and a peroxide, e.g., cumyl hydroperoxide.

A process for preparing aryl substituted aliphatic carboxylic acids or their alkyl esters is disclosed in U. S. Pat. No. 5,315,026. A 1-aryl substituted olefin is reacted with carbon monoxide in the presence of water or an alcohol at a temperature between about 25° C. and about 200° C. A mixture useful as a catalyst is a palladium compound and a copper compound with at least one acid-stable ligand. Ligands which may be used include monodentate or multidentate electron-donating substances such as those containing elements P, N, O and the like, and those containing multiple bonds such as olefinic compounds. Examples of such acid-stable ligands are trihydrocarbylphosphines, including trialkyl- and triarylphosphines, such as tri-n-butyl-, tricyclohexyl-, and triphenylphosphine; lower alkyl and aryl nitriles, such as benzonitrile and n-propionitrile; ligands containing pi-electrons, such as an allyl compound or 1,5-cyclooctadiene; piperidine, piperazine, trichlorostannate(II), and acetylacetonate; and the like.

U.S. Pat. No. 5,536,870 describes the preparation of substituted olefins by the palladium-catalyzed coupling of vinyl or substituted vinyl compounds with organic halides, and also the formation of carboxylic acids and esters from such substituted olefins. The substituted olefinic compounds are formed by reacting an organic halide with a vinyl or substituted vinyl compound in the presence of a catalytically effective amount of palladium or a salt of palladium having a valence of zero, 1 or 2, and a tertiary phosphine ligand such as neomenthyldiphenylphosphine. This reaction is carried out in the presence or absence of a solvent such as acetonitrile, tetrahydrofuran, dioxane, or dimethylformamide. An important utility of the substituted olefins formed in this manner is the subsequent conversion of such substituted olefins to carboxylic acids or derivatives thereof such as salts or esters (e.g., profen compounds) by carbonylation with carbon monoxide using catalytic systems and reaction conditions described in U.S. Pat. No. 5,536,870.

SUMMARY OF THE INVENTION

This invention provides, inter alia, process technology enabling the vinylation reaction to be performed at high reaction rates with high conversions and good selectivities. Moreover, this process technology makes it possible to conduct the vinylation reaction efficiently in plant-sized equipment.

In one of its embodiments, this invention provides a process for preparing an olefinic compound of the formula

(I)

where Ar is aryl, substituted aryl, heteroaryl, substituted heteroaryl, aralkyl (especially benzyl), or substituted aralkyl (especially substituted benzyl), and $R^1$, $R^2$, and $R^3$ are the same or different and are selected from hydrogen atoms, hydrocarbyl groups, functionally-substituted hydrocarbyl groups, and halogen atoms. The process comprises reacting A) at least one organic halide of the formula

(II)

where Ar is as defined above and X is a halogen atom of atomic number greater than 9, a diazonium group or triflate or other leaving group; with B) at least one olefinic compound of the formula

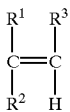
(III)

where $R^1$, $R^2$, and $R^3$ are as previously defined herein. The reaction is conducted in a liquid reaction medium composed of a mixture of (i) at least one liquid organic solvent/diluent and (ii) at least one secondary and/or tertiary amine capable of serving as a hydrogen halide acceptor. The reaction is conducted in the presence of a catalytically effective amount of a catalyst system formed from (a) palladium and/or at least one compound of palladium in which the palladium has a valence of zero, 1 or 2, and (b) a tertiary phosphine ligand of the formula $$R^4R^5R^6P \qquad (IV)$$

where $R^4$, $R^5$, and $R^6$ are the same or different and are selected from alkyl, aryl, substituted aryl, heteroaryl, substituted heteroaryl, aralkyl, substituted aralkyl, cycloalkyl, and substituted cycloalkyl, at least one of $R^4$, $R^5$, and $R^6$ being aryl or substituted aryl. In addition, a small reaction-accelerating amount of water is included or present in the reaction mixture. The reaction is performed under conditions such that olefinic compound of Formula (1) above is formed. Preferably at least one of $R^4$, $R^5$, and $R^6$ is aryl or substituted aryl and at least one of $R^4$, $R^5$, and $R^6$ is cycloalkyl or substituted cycloalkyl.

The small, controlled amount of water used (added and/or maintained) in the vinylation process of this invention is in the range of about 0.5 to about 5.0 weight percent of the total weight of the above reaction mixture and serves as a reaction accelerator thereby enabling formation of the desired products in much shorter times than reaction times reported in *Organometallics*, 13, 2405 (1994). In addition, these beneficial rate increases are achieved in reaction mixtures which do not contain large amounts of inorganic hydrogen halide acceptors or large amounts of water without use of inorganic hydrogen halide acceptors such as described in U.S. Pat. Nos. 5,136,069 and 5,243,068. In fact, excessive amounts of water actually decrease reaction rate as compared to rates achievable by the practice of this invention. In fact, in some cases an excessive amount of water can actually cause the reaction to stop without reaching completion. Thus when conducting the vinylation reaction of this invention it is important to avoid the inclusion or build up of an excessive amount of water in the system. In all cases this invention utilizes reaction mixtures which contain no more than about 5 weight percent of water. Moreover within the range of about 0.5 to 5 weight percent water there is often an optimum amount of water which gives the highest or peak reaction rate which falls off if more or less water is used. This optimum amount of water may vary depending upon the identity and proportions of the ingredients used in forming the reaction mixture. Thus in any given situation it may be desirable to perform a few preliminary experiments with the particular reaction to be conducted, wherein the amount of water is varied within the range of about 0.5 to about 5 wt % to locate the optimum rate-enhancing amount of water in the mixture. Preferably, the amount of water used will be insufficient to form a second liquid phase (i.e., a separate water layer) in a mixture consisting of (i) the amount of the liquid organic solvent/diluent(s) selected for use, (ii) the selected amount of the liquid secondary and/or tertiary amine(s) selected for use, and (iii) the selected amount of water, when such mixture is agitated for 10 minutes at 25° C. and allowed to stand for 15 minutes at the same temperature. Thus when conducting the process on a large scale with recycle of solvent(s) and amine, the amount of water carried over from product workup should be monitored and/or controlled such that the water content of the reaction mixture remains at or below about 5 wt % of the total weight thereof. Conversely if the amount of recycled water is insufficient to maintain the desired water content in the reaction mixture, additional water should be added to bring the water content up to the desired amount within the foregoing range.

In conducting the preferred embodiment wherein the mixture of (i) liquid organic solvent/diluent(s), (ii) secondary and/or tertiary amine(s), and (iii) water does not separate into a two-phase system, the liquid mixture of these components may nonetheless be hazy or cloudy, but a distinct coalesced second liquid phase does not exist as a separate layer in such liquid mixture.

Another embodiment of the invention involves converting the olefinic compound of Formula (I) into a carboxylic acid or carboxylic acid derivative (e.g., salt or ester) by means of a carboxylation reaction described hereinafter.

The above and other embodiments will be apparent from the ensuing description and appended claims.

GLOSSARY OF TERMS

In the specification and claims hereof, the meaning of the substituent groups is as follows:

"alkyl" means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl, and the like; and "$C_1$ to $C_6$ alkyl" means alkyl with 1 to 6 carbon atoms;

"cycloalkyl" means cyclic alkyl having 3 to 7 carbon atoms and includes cyclopropyl, cyclobutyl, cyclopentyl, cyclohexyl, cycloheptyl and like saturated cycloalkanes.

"substituted cycloalkyl" means cyclopropyl, cyclobutyl, cyclopentyl, cyclohexyl, or cycloheptyl substituted by at least one substituent selected from aroyl (as defined below), halogen (chlorine, bromine, fluorine or iodine), amino, nitro, hydroxy, alkyl, alkoxy (which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy and decyloxy), cycloalkyloxy including cyclopentyloxy, cyclohexyloxy and cycloheptyloxy, aryloxy and substituted aryloxy including phenoxy and phenoxy substituted with halo, alkyl, alkoxy and the like, haloalkyl which means straight or branched chain alkyl having I to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-diibromoethyl, 2,2-difluoroethyl, 3,3- dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl, 2,2,3,3-tetrafluoropropyl and the like;

"aryl" means phenyl, naphthyl, or biphenyl;

"substituted aryl" means phenyl, naphthyl, or biphenyl substituted by at least one substituent selected from aroyl (as defined below), halogen (chlorine, bromine, fluorine or iodine), amino, nitro, hydroxy, alkyl, alkoxy (which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy and decyloxy), cycloalkyloxy including cyclopentyloxy, cyclohexyloxy and cycloheptyloxy, aryloxy and substituted aryloxy including phenoxy and phenoxy substituted with halo, alkyl, alkoxy and the like, haloalkyl which means straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoro-ethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-diibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl and the like;

"cycloalkylalkyl" means a straight or branched chain alkyl moiety having 1 to 8 carbon atoms that is substituted by a cycloalkyl group having 3 to 7 carbon atoms, and includes, for example, cyclopropylcarbinyl (i.e., carbinyl may also be termed methyl in this context), cyclobutylcarbinyl, cyclopentylcarbinyl, cyclohexylcarbinyl, cycloheptylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 6-cyclopropylhexyl, 6-cyclohexylhexyl and the like;

"aralkyl" means a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like;

"substituted aralkyl" means aralkyl substituted by at least one substituent selected from aroyl (as defined below), halogen (chlorine, bromine, fluorine or iodine), amino, nitro, hydroxy, alkyl, alkoxy (which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy and decyloxy), cycloalkyloxy including cyclopentyloxy, cyclohexyloxy and cycloheptyloxy, aryloxy and substituted aryloxy including phenoxy and phenoxy substituted with halo, alkyl, alkoxy and the like, haloalkyl which means straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-diibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl, 2,2,3,3-tetrafluoropropyl and the like;

"alkylthio" means a divalent sulfur with alkyl occupying one of the valencies and includes the groups methylthio, ethylthio, propylthio, butylthio, pentylthio, hexylthio, octylthio and the like;

"heteroaryl" means 5 to 10 membered mono- or fused-hetero-aromatic ring which has at least one heteroatom and includes those selected from nitrogen, oxygen and sulfur, and includes, for example, 2-furyl, 3-furyl, 2-thienyl, 3-thienyl, 2-pyridyl, 3-pyridyl, 4-pyridyl, pyrazolyl; imidazolyl, pyrimidinyl, pyridazinyl, pyrazinyl, benzimidazolyl, quinolyl, oxazolyl, thiazolyl, indolyl, and the like;

"substituted heteroaryl" means 5 to 10 membered mono- or fused-heteroaromatic ring which has in the ring at least one heteroatom selected from nitrogen, oxygen and sulfur, and which ring is substituted by at least one substituent selected from halogen, amino, nitro, hydroxy, alkyl, alkoxy and haloalkyl on the above-mentioned heteroaromatic nucleus;

"alkanoyl" means alkanoyl having 2 to 18 carbon atoms and includes, for example, acetyl, propionyl, butyryl, isobutyryl, pivaloyl, valeryl, hexanoyl, octanoyl, lauroyl, stearoyl and the like;

"aroyl" means benzoyl or naphthoyl;

"substituted aroyl" means benzoyl or naphthoyl substituted by at least one substituent including those selected from halogen, amino, nitro, hydroxy, alkyl, alkoxy and haloalkyl on the benzene or naphthalene ring;

"heteroarylcarbonyl" means that the heteroaryl moiety is 5 to 10 membered mono- or fused- heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, benzimidazolyl-carbonyl, and the like;

"substituted heteroarylcarbonyl" means the above-mentioned heteroarylcarbonyl which is substituted by at least one substituent selected from halogen, amino, nitro, hydroxy, alkoxy and haloalkyl on the heteroaryl nucleus; and includes, for example, 2-oxo-1,3-dioxolan-4-ylmethyl, 2-oxo-1,3-dioxan-5-yl and the like;

"ivinyl" means an unsaturated substituent having at least one unsaturated double bond and having the formula $CH_2=CH-$;

"substituted vinyl" means the above vinyl substituent having at least one of the protons on the terminal carbon atom replaced with alkyl, cycloalkyl, cycloalkylalkyl, aryl, substituted aryl, heteroaryl or substituted heteroaryl;

"hydrocarbyl" means a univalent hydrocarbon group containing up to about 24 carbon atoms (i.e., a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, aralkyl, alkyl-substituted aralkyl, and cycloalkyl-substituted aralkyl; and "functionally-substituted hydrocarbyl groups" means a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl.

"vinylation" means a reaction in which at least one organic halide (Formula (II) above) (preferably aryl halide, or substituted aryl halide or a combination of at least one aryl halide and at least one substituted aryl halide) is used as a reactant in the reaction with an olefinic compound (Formula (III) above).

Also, as used herein, "liquid" means that the material referred to exists in the liquid state of aggregation at 20° C. (and preferably at temperatures below 20° C.).

FURTHER DETAILED DESCRIPTION

Vinylation Reaction

Preferably, in the compounds of the above formulas, Ar is unsubstituted or substituted aryl, $R^1$, $R^2$, and $R^3$ are hydrogen, $C_1$ to $C_6$ alkyl, substituted or unsubstituted phenyl or trifluoromethyl. The aryl or substituted aryl group of the aryl halide or substituted aryl halide is preferably phenyl substituted with alkyl, naphthyl substituted with alkoxy, phenyl substituted with aryloxy (especially phenoxy or alkylphenoxy), aryl substituted with fluoro, or phenyl substituted with aroyl, and the halogen atom of the aryl or substituted aryl halide is preferably a bromine atom. Examples of substituted aryl halides include those wherein the aryl group of the substituted aryl monohalide is an isobutylphenyl group, a methoxynaphthyl group, a phenoxyphenyl group, a fluorobiphenylyl group, a benzoylphenyl group, and where the halogen atom is a chlorine atom, an iodine atom, or most preferably a bromine atom. Preferred cases thus include those where Ar is phenyl substituted with alkyl (e.g., isobutyl) or naphthyl substituted with alkoxy (e.g., methoxy), and $R^1$, $R^2$, and $^3R$ are hydrogen, methyl or trifluoromethyl, especially hydrogen.

Preferred olefinic compounds of Formula (III) above are those in which $R^3$ is a hydrogen atom, and vinyl olefins in which $R^1$ is a hydrogen atom or a $C_1$ to $C_6$ alkyl group, and $R^2$ and $R^3$ are hydrogen atoms are especially preferred. Ethylene is the most preferred olefinic reactant.

A variety of liquid solvent/diluents free of functionality that would prevent or materially impair, inhibit or otherwise materially interfere with the vinylation reaction can be used in forming the liquid medium. Examples include tetrahydrofuran, 1,4-dioxane, diglyme, triglyme, acetonitrile, propionitrile, benzonitrile, N,N-dimethylformamide, N,N-dimethylacetamide, dimethylsulfoxide, nitrobenzene, sulfolane, acetone, butanone, and cyclohexanone. Additional solvents that may be considered for use are referred to in U.S. Pat. No. 5,243,068 all disclosure of which is incorporated herein by reference. The solvent/diluent should have at least a measurable polarity at a temperature in the range of 20 to 25° C., and preferred solvent/diluents are one or more aprotic solvents each having a dielectric constant of at least about 10 (especially 10 to 30) at a temperature in the range of 20 to 25° C. From the cost-effectiveness standpoint, hydrocarbyl ketones with 4 or more carbon atoms in the molecule (e.g., 4 to about 8) are preferable. Examples include diethyl ketone, methyl isobutyl ketone, 2-pentanone, 2-hexanone, 3-hexanone, 2,3-pentanedione, 2,4-pentanedione, cyclohexanone, and like liquid ketones, as well as mixtures of two or more such ketones. In a preferred embodiment the ketone or mixture of ketones used will have boiling temperatures above the boiling temperature of the amine(s) used. The vinylation reaction inherently tends to be an exothermic reaction, and the use of diluents having a dielectric constant of in the range of about 10 to about 30 (as measured at 20 to 25° C.), such as a ketone meeting this qualification provides a readily controllable reaction.

Use can be made of any liquid secondary or tertiary amine that is free of functionality that would prevent or materially impair, inhibit or otherwise materially interfere with the vinylation reaction and that has sufficient basicity to serve as a hydrogen halide acceptor for the HCl, HBr and/or HI, formed in the vinylation reaction. Preferred are liquid secondary and more preferably, liquid tertiary amines. The amines may be polyamines but in most cases monoamines are preferable. Suitable secondary and tertiary amines that can be used are also referred to in U.S. Pat. No. 5,243,068 which has been incorporated herein. When using the preferred workup procedure referred to hereinafter, the secondary or tertiary amine(s) used are those that boil below the boiling temperature of each of the polar solvent/diluent(s) used in forming the liquid medium for the reaction. The amines may be polyamines such as for example, N,N,N',N'-tetramethylethylenediamine (b.p. ca. 120–122° C.), but in most cases monoamines are preferable. Among useful liquid amines having suitably low boiling points are diethylamine (bp 55° C.), N,N-dimethylethylamine (bp 36–38° C.), N,N-diethylmethylamine (bp 63–65° C.), diisopropylamine (bp 84° C.), triethylamine (bp ca. 89° C.), dipropylamine (bp ca. 105–110° C.), and di-sec-butylamine (bp ca. 135° C.). Triethylamine is a particularly preferred amine.

The secondary or tertiary amines are used as hydrogen halide acceptors and thus preferably are used in at least a stoichiometric amount relative to the aryl halide being used. However it is possible, though less desirable, to use less than a stoichiometric amount of amine, by allowing the reaction with less than a stoichiometric amount of amine to proceed only part way, and by recycling the reaction mixture for further reaction in the presence of additional amine added thereto.

Typical polar liquid reaction media comprise mixtures formed from (i) at least one liquid ketone, (ii) at least one ketone-soluble tertiary monoamine (usually in an amount of at least one mole per mole of the organic halide), and one or more additional liquid polar solvents such as liquid nitriles and liquid N,N-dialkylalkanamides.

Liquid media formed from diethyl ketone and acetonitrile (e.g. in a weight ratio in the range of 1:9 to 4:1, and more preferably in the range of 1:3 to 3:1) plus triethylamine, or from diethyl ketone and N,N-dimethylformamide (e.g., in a weight ratio in the range of 1:9 to 9:1) plus triethylamine are preferred liquid media for use in this invention.

Liquid media formed from diethyl ketone and triethylamine or from methyl isobutyl ketone and triethylamine are particularly preferred.

As noted above, all such media will contain a reaction accelerating quantity of water in the range of up to about 5 wt %, and in preferred cases, even less than 5 wt % water.

The catalyst system used is formed from (a) palladium and/or at least one compound of palladium in which the palladium has a valence of zero, 1 or 2, and (b) a tertiary phosphine (sometimes referred to herein as "ligand"). The use of salts of palladium in forming the catalysts is preferable because catalyst compositions formed from palladium salts appear to have greater activity than those made from palladium metal itself. Of the salts, palladium(II) salts such as the Pd(II) halides (chloride, bromide, iodide) and Pd(II) carboxylates (e.g., acetate, propionate, etc.) are most preferred.

A highly preferred type of tertiary phosphine used is one or more tertiary phosphine ligands of the formula

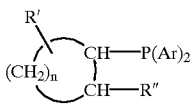

where R' and R" are the same or different and are individually hydrogen, alkyl, aryl or substituted aryl, Ar is phenyl, naphthyl, substituted phenyl or substituted naphthyl and n is an integer from 3 to 6. Preferably, R' and R" are the same or different and are $C_1$ to $C_6$ alkyl, Ar is phenyl or naphthyl and n is 3 or 4. Most preferably, R' is methyl or ethyl, R" is $C_1$ to $C_6$ branched alkyl, Ar is phenyl and n is 4. Especially preferred as the phosphine ligand is neomenthyldiphenylphosphine.

Conditions for the vinylation reaction usually require an equimolar ratio of olefinic compound (Formula (III) above) to organic halide (Formula (II) above), although an excess of olefinic compound is preferred. The palladium catalyst ingredient and the phosphine ligand are typically used at about a ratio of 1 mole of organic halide to 0.0005 mole of palladium or palladium compound. The ligand is present in the same or higher molar proportion as the palladium or palladium compound. It should be noted that levels of (a) palladium metal or palladium compound, and (b) ligand can be substantially higher (up to 10 times). When relatively inactive species of olefinic compound or organic halide (i.e., aryl halide or substituted aryl halide) are employed, for example, highly substituted olefins and/or organic halides bearing strongly electron donating substituents, these higher amounts of catalyst and ligand may be required. Thus the mole ratio of organic halide:Pd:ligand used will generally be a suitable ratio within the range of 200–20,000:1:1–20, respectively.

Temperatures of reaction are quite modest, varying from about 25° C. to 200° C. (preferably 60° C. to 150° C.) with pressures (for the gaseous vinyl compounds) being from atmospheric up to about 3000 psi (preferably 300 to 1000 psi). With the preferred catalyst systems and liquid media referred to above, reaction times are unusually short, typically giving complete reaction in the range of 1 to 24 hours, typically in the range of about 2 to about 6 hours. Higher temperatures and lower pressures tend to cause increased by-product formation.

Preferably the vinylation reaction mixtures of this invention have a water content in the range of about 1 to about 3.5 weight percent.

The optimum conditions will depend to some extent upon the identity of the particular ingredients being used. Thus, for example, when forming 6-methoxy-2-vinylnaphthalene (MVN) from 2-bromo-6-methoxynaphthalene (BMN) using ethylene as the olefinic reactant, a palladium (II) salt such as $PdCl_2$ and neomenthyldiphenylphosphine (NMDP) as catalyst or catalyst precursors, a $C_4$–$C_8$ ketone especially diethyl ketone and a, $C_4$–$C_9$ trialkyl amine especially triethylamine as the liquid medium and a reaction accelerating amount of water, the BMN:Pd:NMDP mole ratio is preferably in the range of about 1000–3000:1:2–10, respectively, the mole ratio of amine:BMN can be in the range of 0.1–2:1 and preferably is in the range of 1–2:1 respectively, the mole ratio of ketone:amine is preferably in the range of 1.0–4.0:1 respectively, the weight of water based on the total weight of BMN+ketone+amine+Pd catalyst ingredient+tertiary phosphine ligand+water is preferably in the range about 1 to about 3.5 wt %, the reaction temperature is typically in the range of about 60 to about 150° C. and preferably in the range of about 80 to about 110° C., and the pressure of the ethylene used is preferably in the range of about 400 to about 1000 psig. Under these conditions, reaction is complete within the range of about 1 to about 24 hours, and oftentimes within about 2 to about 6 hours, with conversions and yields of MVN (both based on BMN used) of 70% to 99%, such as, for example, about 95% conversion and about 85% yield. It is to be clearly understood that the foregoing conditions given in this paragraph are, as stated, preferred conditions for carrying out the specified reaction. On the basis of the information presented in this disclosure, one skilled in the art could readily operate outside of the ranges given in this paragraph, and still achieve good performance in accordance with this invention. Thus this invention is not limited to use of the conditions given in this paragraph, and it is within the scope of this invention when performing the specified reaction to depart from any one or more of such ranges, whenever deemed necessary or desirable in any given situation.

For best results, the overall vinylation reaction mixture is essentially solids-free when at reaction temperatures, except for some precipitation of palladium and formation of some solid co-products such as amine-hydrohalide salt and products formed by interaction of the aryl halide or substituted aryl halide (e.g., BMN) with the vinylated product (e.g., MVN), and/or by dimerization of such vinylated product that may occur as the reaction proceeds. Since the reaction tends to be exothermic, it is desirable to utilize reactors equipped with internal cooling coils, cooling jackets or other highly effective cooling means to ensure suitable temperature control.

A few examples of desirable laboratory reaction parameters in the reaction of BMN with ethylene using $PdCl_2$ and NMDP at 95° C. and 420 psig ethylene are as follows:

a) NMDP:Pd mole ratios in the 5:1–6:1 range give relatively fast reaction rates.

b) BMN:Pd:NMDP mole ratios of 2000:1:6, 2500:1:5 and 3000:1:10 give high conversions and good yields; ratios of 3000:1:6 and 3500:1:5 are operable but give lower conversions.

c) As agitator speeds increase from 300 to 1500 rpm, reaction times to completion decrease by almost two hours.

d) At a BMN:Pd:NMDP mole ratio of 2000:1:6, ethylene pressures ranging from 190 psig to 955 psig at 95° C. give good results. Thus at 190 psig the yield of MVN was 86%, and at 900 psig the yield was 96%. At the higher pressures of the range, reaction times were shorter and the amount of solid by-products formed was less.

e) At a BMN:Pd:NMDP mole ratio of 2000:1:6, MVN yields are higher and the amount of solid by-products formed is lower, when using BMN concentrations at the lower end of the range of 20 to 35 wt % than at the higher end of the range.

f) Reactions at a BMN:Pd:NMDP mole ratio of 2000:1:6 using 1.6 wt % water as reaction accelerator proceed at a higher reaction rate at 95° C. than at 85° C.

g) Maximum rate of reaction is achieved at about 3 wt % water when operating at 95° C., 420 psig ethylene, BMN:Pd:NMDP mole ratio of 2000:1:6, at 30 wt % BMN concentration. The rate is about 150% of the rate when no added water is present. Under these particular conditions, water levels greater than about 4% caused the reaction to stop at less than complete conversion.

h) Use of recycled DEK solvent in four successive runs was successful; no new impurities were found in the MVN product solutions after four recycles. Addition of makeup water when needed to maintain the desired level of water in the reaction mixture is desirable in order to achieve the beneficial reaction accelerating effect of the water from run to run.

Workup of Vinylation Product Mixture

If desired, the olefin of Formula (I) formed in the reaction mixture can be readily separated by various means, e.g., distillation or extraction with a non-polar solvent, e.g., liquid hydrocarbons having from 5 to 12 carbon atoms, both linear and branched, such as hexane.

When the olefinic compound of Formula (I) is to be used in forming a carboxylic acid, or salt or ester thereof, a particularly preferred procedure for working up the vinylation reaction product mixture formed as above and containing the olefinic compound of Formula (I) preparatory to conduct of the carboxylation reaction is used. This procedure involves (a) the release and recovery of amine from the amine-hydrohalide coproduct formed during the vinylation reaction by use of a suitably strong inorganic base (i.e., an inorganic base having a base strength greater than the base strength of the amine(s) used as hydrogen halide acceptor(s), such as $K_2CO_3$, $NaHCO_3$, and preferably an even stronger base such as NaOH, KOH, etc., and (b) a solvent exchange procedure wherein the amine is replaced by a solvent such as an ether, especially tetrahydrofuran, to produce a mixed solvent system which contains ketone or other solvent/diluent used in the vinylation reaction, all as described in commonly-owned U.S. application Ser. No. 780,308, filed Jan. 8, 1997, all disclosure of which is incorporated herein.

In conducting these operations, a concentrated aqueous solution of inorganic base such as $K_2CO_3$, $NaHCO_3$, etc., having a base strength greater than that of the amine(s) of the amine-hydrohalide, and more preferably a concentrated aqueous alkali metal hydroxide solution, is mixed with at least a portion (preferably, all) of the reaction mixture to convert the amine-hydrohalide therein to free amine and inorganic halide salt such as alkali metal halide, and to form (i) an aqueous phase containing dissolved halide salt, and (ii) an organic phase comprising olefinically-substituted aromatic compound, amine, and one or more of the polar organic solvents. Although well known to those skilled in the art, it is deemed necessary, or at least prudent, to point out that because the conversion of the amine-hydrohalide to free amine and, say, "alkali metal halide" is conducted in the presence of water, the "alkali metal halide", or at least a substantial proportion thereof, exists in ionic form while dissolved in the water. Thus according to known chemical principles, the water contains alkali metal cations and halide anions. However chemists would commonly refer to this as forming alkali metal halide because upon removal of water, alkali metal halide would indeed exist as such. Thus when referring in the specification and claims hereof to converting the amine-hydrohalide to free amine and halide salt such as alkali metal halide, it is to be understood that this means that resulting mixture contains the liberated amine and the halide salt in whatever chemical forms they exist in the environment and under the conditions used.

The concentrated alkali metal hydroxide solution may be formed by dissolving alkali metal oxide or hydroxide, or both, in water. The preferred alkali metal oxides and/or hydroxides are those of sodium or potassium, or mixtures thereof. These are plentiful and less expensive than the lithium, rubidium and cesium oxides and hydroxides, which could, however, be used. If desired, the sodium hydroxide or potassium hydroxide solution may be formed from small or even trace amounts of one or more of these other more expensive alkali metal oxides and/or hydroxides together with large amounts of the sodium and/or potassium oxides and/or hydroxides. Again it is to be noted that in the aqueous solution, the alkali metal hydroxide is ionized so that the solution contains, according to well established chemical principles, alkali metal cations and hydroxyl anions. Therefore, reference in the specification and claims hereof to alkali metal hydroxide solution means that the alkali metal hydroxide is in whatever chemical form it exists while in a concentrated aqueous solution.

Whether conducted in stages or all at once, ultimately at least a stoichiometric amount of the inorganic base should be, and in most cases is, employed relative to the amount of amine-hydrohalide present in the reaction mixture.

As to the concentration of these inorganic base solutions, it is desirable to use solutions that contain the equivalent of at least about 10 weight percent of the base, such as alkali metal hydroxide, being used. Saturated aqueous alkali metal hydroxide solutions can be used, but typically the concentration will be at least slightly less than this. Preferred aqueous solutions contain the equivalent of about 20 to about 50 wt % of sodium hydroxide. Particularly preferred aqueous solutions contain the equivalent of about 23 to about 27 wt % of sodium hydroxide. Most preferred is 25 wt % sodium hydroxide aqueous solution.

Preferably the aqueous solution of inorganic base such as alkali metal hydroxide is used in an amount that produces an alkali metal halide solution containing the equivalent of at least about 30 wt % of sodium bromide, and more preferably the equivalent of at least about 40 to 50 wt % of sodium bromide, as this makes the ensuing phase separation easier if the aqueous phase has the higher densities of such concentrated solutions. In addition, less of the organic solvent/diluent(s) and amine(s) are soluble in the aqueous phases having such higher metal halide concentrations, and thus solvent losses are thereby reduced.

The conditions for the mixing of the inorganic base solution such as alkali metal hydroxide solution with the vinylation reaction mixture are not critical. All that is required is to ensure that these materials are sufficiently well mixed so that intimate contact is established between these materials. Temperatures will typically be in the range of about 40 to about 70° C., but other temperatures may be used. Agitation periods in the range of about 5 to about 15 minutes will normally suffice, but longer periods of up to 30 minutes or more (e.g., one hour or more) can be used, if desired.

After mixing, the resulting mixture is allowed or caused to separate into the organic and aqueous phases, usually by allowing the mixture to stand in a quiescent state. Standing periods of one hour or less are usually sufficient. In fact, when treating a vinylation reaction mixture with sufficiently concentrated sodium hydroxide solution to produce an aqueous phase containing 40–45 wt % of sodium bromide, the phases separate quickly, e.g., in as little as 15 minutes. Moreover the phase interface is distinct and easy to detect since oligomeric coproducts tend to float on top of such a concentrated aqueous phase. Then the phases are separated from each other, for example by decantation or, more usually, by draining off the lower aqueous layer.

Next, substantially all of the amine is distilled from the remainder of the organic phase under low temperature and pressure conditions that suppress thermal oligomerization of the olefinically-substituted aromatic compound contained in the residual liquid phase.

Residual amine if present in excessive amounts in the remainder of the organic phase after distillation can have adverse effects upon an ensuing carboxylation reaction. For example, excessive amounts of such residual amine can cause an ensuing carboxylation reaction to stop prematurely with consequent loss of conversions and yields. The amount of such residual amine in the remainder of the organic phase after distillation that can be tolerated in an ensuing carboxylation may vary depending upon such factors as the makeup of the organic phase, the identity of olefinically-substituted aromatic compound contained therein, and the conditions to be used in the carboxylation reaction. Thus in any given situation it may be desirable to perform a few preliminary experiments to determine the amount of amine that can be tolerated without significant adverse effects. Thus sufficient amine is removed such that residual amine, if any, remaining in the remainder of the organic phase does not cause (a) more than about a 5% reduction in conversion of olefinically-substituted aromatic compound contained in the remainder of such organic phase, and (b) more than about a 5% loss of yield of carboxylated product in the ensuing carboxylation as compared to an identical carboxylation of another portion of the same original organic phase from which the amine has been rigorously removed to the extent possible without significantly reducing the olefinically-substituted aromatic compound content of the organic phase. Preferably the amount of residual amine, if any, remaining in the remainder of the organic phase is sufficiently small so that (a) no more than about a 1% reduction in conversion of olefinically-substituted aromatic compound contained in the remainder of such organic phase, and (b) no more than about a 1% loss of yield of carboxylated product in the ensuing carboxylation will occur as compared to an identical carboxylation of another portion of the same original organic phase from which the amine has been rigorously removed to the extent possible without significantly reducing the olefinically-substituted aromatic compound content of the organic phase. To ensure no material adverse effects of amine on an ensuing carboxylation reaction, residual amounts of amine are preferably maintained below about one (1) percent by weight of the distilland remaining after the distillation of amine therefrom.

If an ensuing carboxylation reaction is to be performed, preferably, liquid organic makeup solvent is mixed with the liquid mixture during or after the distillation of the amine whereby the liquid mixture for carboxylation further comprises at least a portion (preferably, all) of the distilland and the makeup solvent. While various solvents may be used, the makeup solvent preferably comprises at least one ether, preferably a liquid cyclic monoether such as tetrahydrofuran, methyltetrahydrofuran, tetrahydropyran, or etc., or a cyclic diether such as 1,3-dioxolane, 1,4-dioxane, or etc., or a mixture of such materials with or without one or more acyclic ethers such as diethyl ether, methyl tert-butyl ether, or the like. The most preferred makeup solvent is tetrahydrofuran as this material appears to exert a rate enhancing effect upon the carboxylation reaction. It is expected that at least some alkyl-substituted tetrahydrofurans may also behave in this manner.

Carboxylation

A further embodiment of the present invention is one in which the olefinic compound of Formula (I) can be used with or without isolation (preferably without isolation, but with use of a workup procedure of the type just described) from the reaction mixture in the catalytic carboxylation step to produce compounds of Formula (V).

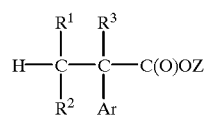

(V)

where Ar, $R^1$, $R^2$, and $R^3$ are as previously defined, and Z is a hydrogen atom, an alkali metal atom (preferably Na or K), a hydrocarbyl group (preferably $C_1$–$C_6$ alkyl), or a functionally-substituted hydrocarbyl group. By suitable modifications of or additions to the carboxylation procedure now to be described, compounds of Formula (V) can be produced in which Z can be any of a wide variety of other groups, non-limiting exemplifications of which include ammonium, quaternary ammonium, one-half equivalent of a divalent metal atom, one-third equivalent of a trivalent metal cation, and so on.

The catalytic carboxylation of the compound of Formula (I) is effected with carbon monoxide and water and/or alcohol, and is conducted, at a temperature between about 25° C. and about 200° C., preferably about 25°–120° C., and most preferably about 25°–100° C. Higher temperatures can also be used. The best yields are obtained when the temperature is maintained at a relatively low level throughout the reaction.

The partial pressure of carbon monoxide in the reaction vessel is at least about 1 atmosphere (0 psig) at ambient temperature (or the temperature at which the vessel is charged). Any higher pressures of carbon monoxide can be used up to the pressure limits of the reaction apparatus. A pressure up to about 3000 psig is convenient in the process. More preferred is a pressure from 0 to about 3000 psig at the reaction temperature and most preferred is a pressure from 0 to about 1000 psig. It should be noted that the presence of oxygen is undesirable in the hydrocarboxylation reaction of this invention. Hence, an atmosphere of 100% carbon monoxide is most preferred to carry out this process. Various inert gases can, however, be incorporated in the reaction mass (nitrogen, argon, etc.), the only criterion being that the process should not be slowed to the point of requiring exceptionally long periods to complete the reaction.

As noted above, the carboxylation is conducted in the presence of an appropriate amount of water or aliphatic alcohol. Strictly speaking, when the reaction is conducted in the presence of water it is a hydrocarboxylation reaction, and when conducted in the presence of an alcohol it can be termed a hydrocarbalkoxylation reaction. Consequently, unless otherwise qualified or specified, the term "carboxylation" is used herein in a generic sense to denote both hydrocarboxylation (using water) and hydrocarbalkoxylation (using an alcohol).

In the case of hydrocarboxylation of MVN, at least about one (1) mole of water per mole of the MVN should be used, and about four moles of water per mole of the MVN is typically employed. It is worth noting that an excessive amount of water can inhibit or even kill the reaction. The effect of large excesses of alcohols in the hydrocarbalkoxylation of MVN has not been studied in detail, but it would appear prudent to avoid use of excessive amounts. Thus amounts in the range of up to about 10 wt % in the reaction mixture are suggested. In carboxylation reactions with other compounds of Formula (I), an excess amount of water and/or alcohol may sometimes be used. In such cases, although possibly there may be no real upper limit to the amount of water or alcohol except that imposed by practicality (e.g. the size of the reaction vessel, and the kinetics of the reaction), an amount up to about 100 moles, and preferably up to about 50, moles per mole of the compounds of Formula (I) may be considered for use in the process, and an amount from about 2 to about 24 moles of water or alcohol per mole of the such olefinic compound is more preferred. The product of the reaction is a carboxylic acid (where Z in Formula (V) is a hydrogen atom) or carboxylic acid ester (where Z in Formula (V) is alkyl or substituted alkyl).

The present invention embraces the formation of any racemates and individual optical isomers of the compounds of Formula (V) having a chiral carbon atom. For example, when compounds of Formula (V) wherein the acid is 2-(6-methoxy-2-naphthyl)propionic acid, are subjected to resolution as taught in U. S. Pat. No. 4,246,164 (incorporated herein by reference), the analgesic compound naproxen is produced.

If desired, any alcohol which produces an ester of the carboxylic acid may be used in the practice of this invention. In a preferred embodiment, the $C_1$ to $C_6$ aliphatic alcohols are used. Examples of the alcohols to be used in this embodiment include methyl alcohol, ethyl alcohol, n-propyl alcohol, isopropyl alcohol, n-, iso-, sec-, and tert-butyl alcohols, the pentyl alcohols, (isoamyl alcohol, especially to form the ester of racemic 2-(6-methoxy-2-naphthyl) propionic acid), the hexyl alcohols, etc. Methyl alcohol is highly preferred, and ethyl alcohol is most highly preferred. Other alcohols, glycols, or aromatic hydroxy compounds may also be used. In the broadest sense, these alcohols provide a source of alkoxide ions for this reaction. However, any other "source of alkoxide ions" may also be used. The source of such alkoxide ions is from a compound selected from the group consisting of $HC(OR_1)_3$, $(R)_2C(OR_1)_2$, $HC(O)OR_1$, $B(OR_1)_3$, $Ti(OR_1)_4$ and $Al(OR_1)_3$ where R is hydrogen or individually the same as or different from $R_1$, and $R_1$ is alkyl or substituted alkyl.

In some cases, the carboxylation reaction is initiated under neutral conditions, i.e., with no added acid. However, at least in the case of hydrocarboxylation of MVN, the inclusion of aqueous HCl in the reaction mixture is deemed important, if not almost essential for most efficient operation. Thus in a preferred embodiment of this invention, the hydrocarboxylation reaction is initiated in the presence of halide ions which are best provided by use of a halogen acid, especially hydrochloric acid, which preferably is an aqueous acid which may for example have a concentration up to about 25 wt %, but preferably has a concentration in the range of about 5 to about 15 wt %, and more preferably in the range of about 7 to about 15 wt %. It is especially preferred to use approximately 10 wt % aqueous HCl. Dilute aqueous HCl also provides water for effecting the hydrocarboxylation. Gaseous HCl can be used to generate hydrochloric acid in situ when water is present when conducting this reaction. HBr and hydrobromic acid may be used, but these appear less effective based on studies conducted to date. Other acids may be considered for use but to date the most effective material is the aqueous hydrochloric acid. Any suitable proportion of hydrochloric acid may be used, typically a reaction accelerating quantity in the range that provides up to 1 mole of hydrogen ion per mole of compound of Formula I, and preferably a quantity that provides in the range of about 0.1 to about 0.5 mole of hydrogen ion per mole of the compounds of Formula I. In the case of carboxylation of MVN, the preferred range is an HCl:MVN mole ratio of about 0.1 to about 0.3, more preferably about 0.15 to about 0.27, and most preferably about 0.18 to about 0.22.

The catalytic carboxylation process of this invention is conducted in the presence of a reaction-promoting quantity of (i) palladium and/or at least one palladium compound in which the palladium has a valence of zero, 1 or 2, (most preferably 2) or (ii) a mixture of (a) palladium and/or at least one palladium compound, and (b) at least one copper compound, with (iii) at least one tertiary phosphine of the type described above. When a copper compound is not employed, the palladium and/or one or more compounds of palladium used in forming the catalyst is/are sometimes collectively referred to herein for convenience as "the Pd ingredient", and the combination of palladium and/or one or more compounds of palladium and one or more compounds of copper used in forming the catalyst (when a copper compound is employed) is sometimes collectively referred to herein for convenience as "the Pd—Cu ingredient".

Thus in general the Pd ingredient and the tertiary phosphine ligand are the same type of materials as described above in connection with the vinylation reaction. Indeed the same preferred types of materials preferred for use in the vinylation reaction are preferred for use in the carboxylation reaction. Fresh catalyst is employed for each such reaction, however. The same species of Pd ingredient and the same species of tertiary phosphine ligand need not be used in these two reactions. Either such component or both of them might differ. Thus, for example, palladium(II) chloride and triphenyl phosphine might be used in the vinylation and palladium(II) acetate and tri-o-tolylphosphine might be used in the carboxylation, or vice versa, but in the most preferred case the same species ($PdCl_2$ and neomenthyldiphenylphosphine) are in fact used in both such reactions.

As in the case of the vinylation reaction, active catalytic species are preferably formed in situ by the addition to the reaction mixture of the individual components. However the catalyst can be preformed externally to the reaction mixture and charged to the reactor as a preformed catalyst composition.

When it is desired to use a copper compound in forming the carboxylation catalyst system, copper complexes such as copper acetylacetonates, copper alkylacetoacetates, or other chelated forms of copper may be used. The preferred copper compounds for this use, however, are salts especially divalent copper salts such as the halides (chloride, bromide, iodide) of copper(II) and the carboxylates of copper(II) such as copper(II) acetate, copper(II) propionate, etc.

In one embodiment, the Pd ingredient and copper compounds are inorganic salts and are added as a preformed complex of, for example, a complex formed from palladium (II) chloride or bromide, copper(II) chloride or bromide and carbon monoxide, or any other similar complex. In a preferred embodiment, active catalytic species are formed in situ by the addition to the reaction mixture of the individual components, i.e., either (i) at least one tertiary phosphine and at least one palladium compound such as the inorganic or carboxylate salts of palladium(II), or (ii) at least one tertiary phosphine, at least one copper compound, and at least one palladium compound such as the inorganic or carboxylic salts of palladium(II) and copper(II). These inorganic salts include the chlorides, bromides, nitrates, and sulfates. Organic palladium and/or copper compounds that may be used include complexes and salts such as the carboxylates, e.g., the acetates or propionates, etc. In one preferred embodiment, neomenthyldiphenylphosphine, copper(II) chloride, and palladium(II) chloride are used and are added individually or together, either simultaneously or sequentially. In another preferred embodiment, neomenthyldiphenylphosphine and palladium(II) chloride are used and are added individually or together, either simultaneously or sequentially.

The Pd ingredient or the Pd—Cu ingredient may be supported on carbon, silica, alumina, zeolite, clay and other polymeric materials, but use of a homogeneous catalyst system is definitely preferable.

The amount of the Pd ingredient or of the Pd—Cu ingredient employed is preferably such as to provide from about 4 to about 8000 moles of the compound of Formula (I) per mole of the Pd ingredient or per total moles of the Pd—Cu ingredient. More preferred is an amount to provide from about 40 to 4000 moles (most preferably about 20 to 2000 moles) of the compounds of Formula (I) per mole of the Pd ingredient or per total moles of the Pd—Cu ingredient. The process of this invention is conducted in the presence of at least one mole of the tertiary phosphine per mole of the Pd ingredient or per total moles of the Pd—Cu ingredient. More preferably, about 1 to about 40 moles of tertiary phosphine are used per mole of the Pd ingredient or per total moles of the Pd—Cu ingredient, and most preferably about 1 to about 20 moles of tertiary phosphine are used per mole of the Pd ingredient or per total moles of the Pd—Cu ingredient.

The presence of a solvent is not always required in the carboxylation reaction, although it is desirable in some circumstances. Those solvents which can be used include one or more of the following: ketones, for example, acetone, methyl ethyl ketone, diethyl ketone, methyl n-propyl ketone, acetophenone, cyclohexanone, and the like; linear, poly and cyclic ethers, for example, diethyl ether, di-n-propyl ether, di-n-butyl ether, ethyl n-propyl ether, glyme (the dimethyl ether of ethylene glycol), diglyme (the dimethyl ether of diethylene glycol), tetrahydrofuran, dioxane, 1,3-dioxolane, and similar compounds; and aromatic hydrocarbons, for example, toluene, ethyl benzene, xylenes, and similar compounds. Alcohols are also suitable as solvents, for example, methanol, ethanol, 1-propanol, 2-propanol isomers of butanol, isomers of pentanol, etc. Esters may also be used, such as ethyl acetate, etc. When an ester or an alcohol is used as solvent, the product is usually the corresponding ester of the carboxylic acid. Most highly preferred are ethers, especially tetrahydrofuran, or mixtures of one or more ethers and one or more ketones, especially mixtures of tetrahydrofuran and diethylketone. When solvents are used, the amount can be up to about 100 mL per gram of the compounds of Formula I, but the process is most advantageously conducted in the presence of about 1 to 30 mL per gram of the compound of Formula (I).

In those specific embodiments of this invention in which an ester is produced, e.g. ibuprofen alkyl ester, the ester may be conveniently converted to the acid (ibuprofen itself) by conventional methods of hydrolysis. Base hydrolysis can also be employed if desired to produce pharmaceutically acceptable salts wherein the cation is sodium, potassium, calcium, hydrogen carbonate or a quaternary ammonium compound.

Workup and Recovery of Carboxylation Product

As noted above, the carboxylation reaction forms a reaction product composition comprising arylcarboxylic acid or substituted arylcarboxylic acid (e.g., racemic 2-(6-methoxy-2-naphthyl)propionic acid or 2-(4-isobutylphenyl) propionic acid, etc.) or an ester thereof (depending on whether water or an alcohol is used in the carboxylation process), and a liquid medium comprising polar organic solvent (preferably ketone or nitrile or mixture thereof), water and/or alcohol, HCl, and preferably at least one ether (e.g., THF, etc.) with a boiling temperature below that of at least one such polar solvent. Also present are catalyst residues and typically some coproducts formed during the reaction.

Pursuant to a preferred embodiment of this invention, the arylcarboxylic acid or substituted arylcarboxylic acid is converted in situ into an inorganic salt of such acid by reaction with an aqueous solution of inorganic base (neutralization step). In addition, when the reaction product composition contains (i) at least one low boiling ether (e.g., THF, etc.) and/or (ii) at least one low boiling polar solvent, where either or both such low boiling materials boil(s) below the boiling temperature of at least one polar solvent contained in the reaction product mixture, some or all of such low boiling materials are distilled from the reaction product composition (distillation step). If the reactor overheads are susceptible to attack by aqueous HCl, the neutralization step should precede or at least be conducted concurrently with the distillation step. On the other hand, if the reactor overheads are formed from acid-resistant materials of construction, the distillation step can precede and/or follow and/or be conducted concurrently with the neutralization step; the HCl in the mixture will not cause excessive corrosion of the reactor overheads even if the distillation precedes the neutralization. In whatever sequence the neutralization step and the distillation step are conducted, a mixture of residual organic phase and an aqueous phase containing dissolved inorganic salt of the arylcarboxylic acid or substituted arylcarboxylic acid remain in the reactor as a distillation residue (distilland or pot residue). These phases are separated from each other. The aqueous phase is then subjected to a distillation, preferably at or near atmospheric pressure, to remove residual organic impurities such as THF. At this point it is desirable to ensure that the residual aqueous phase has a concentration in the range of about 10 and about 35 wt % of dissolved inorganic salt of the arylcarboxylic acid or substituted arylcarboxylic acid and where necessary, adjusting the concentration of the aqueous phase to about 10 and about 35 wt % solution by removal or addition of water. The aqueous solution is then washed (extracted) with substantially non-polar liquid organic solvent (preferably aromatic hydrocarbon solvent, such as toluene or xylene), preferably at least twice. The free arylcarboxylic acid or substituted arylcarboxylic acid is then produced by mixing non-oxidizing mineral acid (e.g., sulfuric acid) with the aqueous phase in the presence of substantially non-polar liquid solvent to form (i) an organic phase composed of a solution of arylcarboxylic acid or substituted arylcarboxylic acid in substantially non-polar liquid solvent and (ii) an aqueous phase. After separating these phases from each other, arylcarboxylic acid or substituted arylcarboxylic acid is crystallized from the substantially non-polar liquid solvent.

The aqueous solution of inorganic base used in the above neutralization step is preferably a 10 to 40 wt % solution of NaOH or KOH. However other inorganic bases that can be used include $Na_2O$, $K_2O$, $Ca(OH)_2$, $CaO$, $Na_2CO_3$, $K_2CO_3$, and other inorganic bases of similar basicity. Such solutions are used in an amount at least sufficient to neutralize the arylcarboxylic acid or substituted arylcarboxylic acid and the HCl present in the reaction product composition.

When the carboxylation reaction is conducted using an alcohol so that an ester of the arylcarboxylic acid or substituted arylcarboxylic acid is present in the reaction product composition, it is preferred to saponify the ester in situ by mixing a concentrated aqueous solution of a strong inorganic base such as NaOH or KOH with the reaction product composition and applying sufficient heat (e.g., heating to a temperature in the range of up to about 80° C.) to form the inorganic salt of the arylcarboxylic acid or substituted arylcarboxylic acid. Then the workup procedure for the carboxylation product as described above is carried out.

The low boiling materials recovered in the initial distillation step are preferably recycled for use in the hydrocarboxylation reaction.

Examples of compounds that can be produced by use of the invention include ibuprofen, 2-(4-isobutylphenyl) propionic acid (U.S. Pat. Nos. 3,228,831 and 3,385,886); 2-(3-fluoro-4-biphenylyl)-propionic acid (also known as flurbiprofen) (U.S. Pat. No. 3,755,427); racemic 2-(6-methoxy-2-naphthyl)propionic acid which can be resolved to d-2-(6-methoxy-2-naphthyl)propionic acid (also known as naproxen) (U.S. Pat. No. 3,637,767); a-dl-2-(3-phenoxyphenyl)propionic acid (also known as fenoprofen) (U.S. Pat. No. 3,600,437); and 2-(3-benzoylphenyl) propionic acid (also known as ketoprofen) (U.S. Pat. No. 3,641,127). As described herein, the bromo precursor of each of the above compounds is reacted with an olefinic compound of Formula (III) (most preferably ethylene) in a one-phase organic liquid medium (most preferably a mixture of a liquid ketone, especially diethyl ketone, and a liquid secondary or tertiary amine such as a trialkyl amine, especially triethyl amine), that also preferably contains the above-described reaction accelerating amount of water) in the presence of a palladium catalyst system (as described herein), which is formed from Pd, Pd(I) salt or preferably Pd(II) salt and a tertiary phosphine ligand such as neomenthyldiphenylphosphine. The amine should be selected to avoid beta hydride elimination under reaction conditions and should not react with the olefin or bromo precursor to any appreciable extent. The bromo precursor substitutes on the ethylene to provide the substituted olefin which is then worked up as described above, and then carboxylated (using carbon monoxide and a palladium-phosphine or a palladium-copper-phosphine catalyst system as described herein) to produce the corresponding acid product (if water forms part or all of the solvent system) or the corresponding ester (if an alcohol such as methyl, ethyl or isoamyl alcohol) is used as all or part of the solvent.

Some of the above reactions can be exemplified as follows:

IBUPROFEN

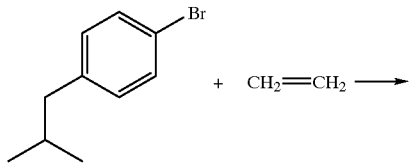

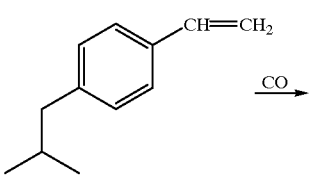

FLURBIPROFEN:

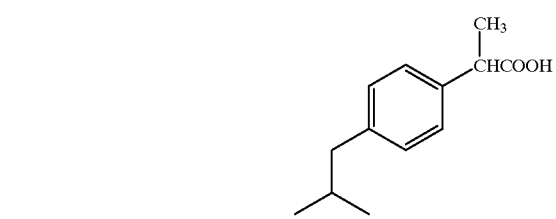

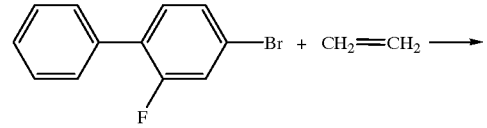

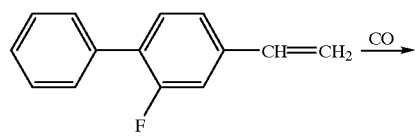

KETOPROFEN:

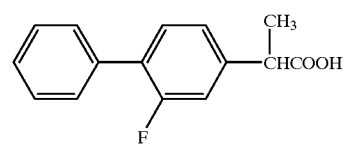

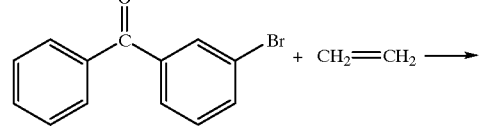

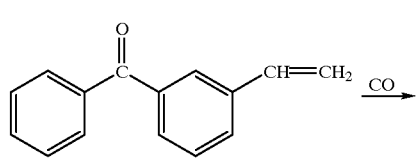

NAPROXEN:

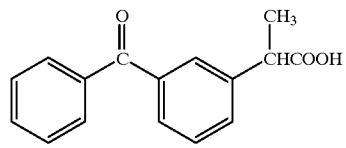

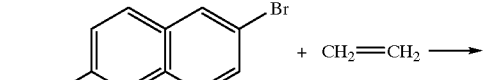

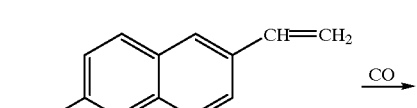

21

-continued

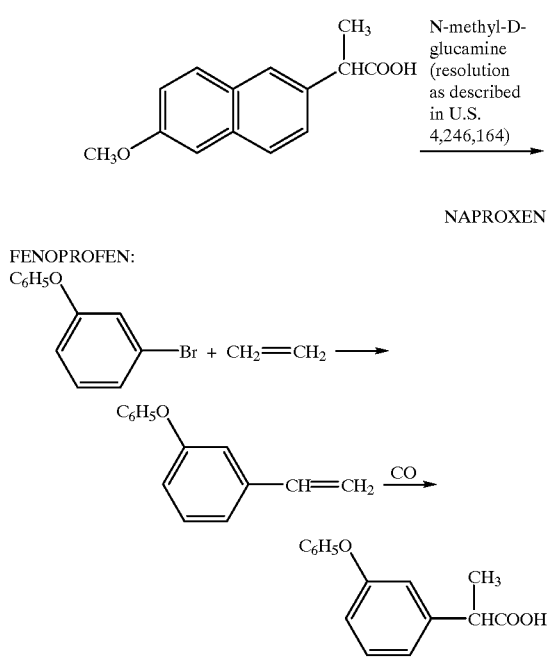

NAPROXEN

FENOPROFEN:

In the above reactions the ethylene pressure should be 50 to 3000 psi (preferably 300 to 1000 psi), the temperature is 30° C. to 200° C. (preferably 60° C. to 150° C.). Temperatures and pressures are selected to minimize by-product formation. Palladium is used (i.e., charged to the reactor) preferably in the form of its salts, (e.g., Pd(II) acetate or chloride) along with a tertiary phosphine ligand as described above, with a cycloalkyldi(alkylphenyl)phosphine such as neomenthylditolylphosphine being preferred, and a cycloalkyldiphenylphosphine such as neomenthyldiphenylphosphine being particularly preferred.

The bromo precursors are frequently commercially available and/or can be readily prepared by those skilled in the art. For example, Aldrich Chemical Company sells m-bromophenol and m-bromoanisole while Albemarle PPC (Thann, France) sells 2-bromo-6-methoxynaphthalene. The bromo precursors of ibuprofen can be prepared by bromination using standard Friedel-Crafts catalysts (e.g., zinc bromide or ferric bromide). The bromo precursor of ketoprofen can be prepared by bromination of methyl benzoate (or a similar lower hydrocarbon ester) using aluminum chloride followed by NaOH hydrolysis, conversion to the acid chloride (e.g., with $SOCl_2$) and reaction with benzene (again, using a Friedel-Crafts catalyst such as $AlCl_3$). The precursor for racemic 2-(6-methoxy-2-naphthyl)propionic acid, viz., 2-bromo-6-methoxyaphthalene, is best made by the process described in commonly-owned U.S. application Ser. No. 780,309, filed Jan. 8, 1997, now U.S. Pat. No. 5,792,886, issued Aug. 11, 1998, all disclosure of which is incorporated herein.

In addition to the profen compounds described above, other profen compounds which can be prepared by use of this invention to convert the corresponding bromo precursors by reaction with ethylene include protizinic acid, tiaprofenic acid, indoprofen, benoxaprofen, carprofen, pirprofen, pranoprofen, alminoprofen, suprofen and loxoprofen.

The following examples are given to illustrate the process of this invention and are not intended as a limitation thereof. Unless otherwise specified all percentages are by weight. Neomenthyldiphenylphosphine is represented by the designation NMDP.

22

EXAMPLE 1

A one-phase mixture was formed from 4-bromoisobutylbenzene (BIBB, 21.3 g 0.100 mol), tetrahydrofuran (THF, 15 mL), triethylamine (TEA, 10.3 g, 0.102 mol), $PdCl_2$, (0.018 g, 0.000102 mol), NMDP (0.200 g, 0.000616 mol), and water (1 mL, 0.0555 mol). The mixture thus contained 7.0% of water based on the total weight THF and water, and 2.2% of water based on the total weight of THF, amine, BIBB and water. The mixture was sealed in an autoclave. The autoclave was purged with ethylene (2×150 psig) and pressured with ethylene (270 psig). The mixture was heated at 110° C. and 540 psig ethylene pressure for 4 hours. Samples taken at 2 and 4 hours were subjected to GC analysis to determine composition.

COMPARATIVE EXAMPLE A

The same procedure as in Example 1 was used except that the addition of water was omitted, the reaction was performed for a total of 6 hours at 110° C. and 530 psig ethylene pressure, and samples for GC analysis were taken after 2, 4 and 6 hours.

Table 1 summarizes the results of the GC analyses of the reaction mixtures of Example 1 and of Comparative Example A. In the Table, the desired vinylation product, 4-isobutylstyrene, is represented by the designation IBS. Dimer represents coproducts, namely 1,1-bis(4-isobutylphenyl)ethene (trace) and 4,4'-diisobutylstilbene (major).

TABLE 1

| | | GC Area % | | |
|---|---|---|---|---|
| Example | Time, Hr. | IBS | BIBB | Dimer |
| 1 | 2 | 70.6 | 26.8 | 2.6 |
| 1 | 4 | 91.0 | 1.6 | 6.6 |
| Comp. A | 2 | 42.7 | 56.4 | 0.8 |
| Comp. A | 4 | 71.3 | 25.3 | 3.4 |
| Comp. A | 6 | 85.6 | 8.5 | 5.8 |

EXAMPLE 2

A 2-liter reactor was charged with 2-bromo-6-methoxynaphthalene (BMN) (284.5 g; 1.2 mol), $PdCl_2$ (0.106 g; 0.0006 mol), NMDP (0.0036 mol), TEA (130 g; 1.28 mol), acetonitrile (ACN) (284.5 g), diethyl ketone (DEK) (284.5 g), and water (30 g). The liquid medium (DEK+ACN+water) thus contained 4.1% water. The water content based on BMN+DEK+TEA+ACN+water was 3.0%. The mixture was heated under an ethylene atmosphere at about 95° C. and at pressures of 470 to 505 psig for 1.5 hours. GC analysis of a sample of the mixture after one hour showed 97.0 area % of 6-methoxy-2-vinylnaphthalene (MVN) and 3.0 area % of BMN. At 1.5 hours the GC showed 98.8 area % of MVN and only a trace of BMN. The conversion (based on BMN) was thus essentially 100%.

EXAMPLE 3

A mixture of DEK (572 g), TEA (127.5 g), and water (30 g) was stirred for 10 minutes at room temperature. The layers were allowed to separate and the lower aqueous phase (2 g) was separated and discarded. The cloudy liquid phase saturated with water was charged to a 2-liter reactor along with BMN (284.5 g; 1.2 mols), $PdCl_2$ (0.106 g; 0.0006 mol), and NMDP (1.17 g; 0.0036 mol). The liquid medium (DEK+TEA+water) thus contained about 4% water. The water content based on BMN+DEK+ACN+water was about 3%. The mixture was heated under an ethylene atmosphere at about 95° C. and at pressures of 470 to 505 psig for 1.5 hours. GC analysis of a sample of the mixture after one hour showed 97.0 area % of 6-methoxy-2-vinylnaphthalene (MVN) and 3.0 area % of BMN. At 1.5 hours the GC showed 98.8 area % of MVN and only a trace of BMN. The conversion (based on BMN) was thus essentially 100%. After completion of the reaction, 25% aqueous caustic solution (223 g) and methylene chloride (198 g) were charged to the reactor and the mixture was stirred for 15 minutes. The contents were transferred to a separatory funnel, and the residual contents in the reactor were washed into the separatory funnel by use of additional methylene chloride. The aqueous layer (308 g) was removed from the funnel. The organic phase was filtered to remove coproduct solids (20 g when dry) and then concentrated to give a yellow solid product (205.6 g).

EXAMPLE 4

A mixture of BMN (284.5 g; 1.2 mols), $PdCl_2$ (0.106 g; 0.0006 mol), NMDP (1.17 g: 0.0036 mol), TEA (130.2 g; 1.29 mol), DEK (570 g), and water (29.2 g) was heated at 95° C. under an ethylene atmosphere at pressures of 430 to 500 psig for 2.5 hours. The amount of water used was 4.0% based on the weight of DEK+TEA+water, and was the amount needed to saturate the DEK–TEA mixture. The GC area % of BMN at 1, 2 and 2.5 hours was 24.9%, 1.7% and 0.1%. The GC area % of MVN at 1, 2 and 2.5 hours was 75.1%, 98.3% and 98.5%.

EXAMPLE 5

A mixture of BMN (237.1 g; 1.0 mol), $PdCl_2$ (0.089 g; 0.0005 mol), NMDP (0.97 g: 0.0030 mol), TEA (151.8 g; 1.5 mols), methyl isobutyl ketone (MIBK) (565 g), and water (29.0 g) was heated at 95° C. under an ethylene atmosphere at pressures of 460 to 500 psig for 4 hours. The amount of water used was 3.9% based on the weight of MIBK+TEA+water. GC analysis of the product mixture showed 97.8 area % of MVN and 0.8 area % of BMN.

EXAMPLE 6

In this run a recycled DEK–TEA solvent mixture, distilled from a prior vinylation reaction mixture after product workup and recovery therefrom, was used in forming this reaction mixture. Thus, 440 g of recycle mixture composed of 81.65 wt % DEK (by GC), 15.51 wt % TEA (by GC), 1.25 wt % THF (by GC) and 2.37 wt % residual water (by Karl Fischer titration) was charged to a reactor. Also charged were BMN (142.3 g; 0.6 mol), $PdCl_2$ (0.053 g; 0.0003 mol), NMDP (0.58 g: 0.0018 mol). More TEA (4.7 g) was added to achieve a TEA:BMN mole ratio of 1.2. The mixture was heated at 94–98° C. under an ethylene atmosphere at pressures of 420 to 450 psig for 2.5 hours. A sample taken at 2 hours showed by GC 93.7 area % MVN and 4.6 area % BMN. At 2.5 hours these values were 98.9% and 0%, respectively. The product mixture was worked up by treatment with 25% aqueous caustic (114 g; 0.71 mol), the aqueous phase (154 g) was removed, and the organic phase was filtered to give a yellow solution.

The reaction rate improvements made possible by the practice of this invention were further demonstrated by a series of 12 vinylation runs conducted in a 2-liter reactor in which the proportions of the ingredients and the reaction conditions used were, except for some small inconsequential differences, the same from run to run, the only independent variable being water content and the amount thereof The reaction mixtures were composed of 300 g of BMN, 529–530 g of DEK, 147–148 g of TEA, 0.112–0.116 g of $PdCl_2$, and 1.23–1.26 g of NMDP. Several runs were conducted with no added water, and the remainder had measured quantities of added water. All reactions were performed at 95° C. under ethylene at 420 to 450 psig. The criterion for reaction rate was maximum rate of ethylene consumption during each reaction. Thus the higher this value, the better. The results of these runs as regards reaction rates are summarized in Table 2.

TABLE 2

| Run No. | Water Content, wt % of Total Reaction Mixture | Maximum Ethylene Consumption, psi/hr |
| --- | --- | --- |
| 1 | None | 38 |
| 2 | None | 38 |
| 3 | None | 39 |
| 4 | 0.8% | 45 |
| 5 | 1.6% | 43 |
| 6 | 1.6% | 49 |
| 7 | 2.25% | 53 |
| 8 | 2.25% | 60 |
| 9 | 3.1% | 58 |
| 10 | 3.1% | 63 |
| 11 | 4.6% | 37 |
| 12 | 5.9% | 42 |

Example 7 illustrates a preferred overall procedure for producing racemic 2-(6-methoxy-2-naphthyl) propionic acid on a large (1000 gallon) scale using fresh DEK. As is well known in the art, the terms or designations "racemic 2-(6-methoxy-2-naphthyl)propionic acid" and "(±)-2-(6-methoxy-2-naphthyl)propionic acid" mean exactly the same thing. For convenience, "sodium racemate" is sometimes used in the following examples to refer to racemic sodium 2-(6-methoxy-2-naphthyl)propionate.

EXAMPLE 7

Vinylation Reaction

To a 1000 gallon reactor are charged 750 kg of BMN, 1305 kg of DEK, 368 kg of TEA, 0.3 kg of $PdCl_2$, 3.1 kg of NMDP, and 37 kg of water. The reactor is sealed, pressured to 100 psig with ethylene and the reactor temperature is adjusted to 95° C. The reactor is then pressured to 425–450 psig with ethylene and held at this pressure until the uptake of ethylene is completed. The reactor is cooled to 60° C. and excess ethylene is vented from the reactor. The reaction typically takes 4–6 hours to go to completion and typically gives a >95% BMN conversion and a MVN yield of 85–95%.

Product Workup and Solvent Exchange

To the reaction product from the vinylation reaction is added 557 kg of a 25 wt % aqueous sodium hydroxide solution. The mixture is stirred for 15 minutes at 50–60° C. and then allowed to stand for 15 minutes. The bottom aqueous solution is drained from the vessel. The organic phase is then subjected to distillation at pressures in the range of 200 mm Hg to 300 mm Hg to distill off TEA to a level at which the weight ratio of TEA:MVN is less than 0.016. After adding THF to the residual organic phase (distilland or pot residue) to form a mixture in which the THF:DEK weight ratio is approximately 1:1, this mixture is filtered to remove solids (palladium catalyst residues and oligomeric or dimeric coproduct).

Hydrocarboxylation Reaction

Charged to a 1000 gallon reactor are a filtered THF–DEK–MVN solution produced as in the above workup procedure containing 550 kg of MVN, 825 kg of DEK, and 825 kg of THF, followed by 0.3 kg of $PdCl_2$, 0.64 kg of $CuCl_2$, 3.1 kg of NMDP, and 200 kg of 10 wt % HCl. The reactor is then pressured to 100 psig with carbon monoxide and the reactor temperature is adjusted to 70° C. The reactor is then pressured to 360 psig with carbon monoxide and held at this pressure until the uptake of carbon monoxide is completed. The reactor is then cooled and the pressure is vented. The reaction typically takes 4–8 hours to go to completion with >95% MVN conversion and a yield of racemic 2-(6-methoxy-2-naphthyl)propionic acid of approximately 90%.

Racemic Product Workup and Recovery

Aqueous sodium hydroxide (25 wt % solution) is added to the reactor to convert the racemic 2-(6-methoxy-2-naphthyl) propionic acid to racemic sodium 2-(6-methoxy-2-naphthyl) propionate, and to neutralize the HCl remaining in the reaction mixture. The THF is then distilled from the reaction mixture at atmospheric pressure. (These neutralization and distillation steps can be reversed if the materials of construction of the reactor overhead are resistant to HCl). The resultant aqueous phase is separated from the organic phase which is composed mainly of DEK and impurities. The residual organics (e.g., DEK) contained in the aqueous phase are distilled from the aqueous racemic sodium 2-(6-methoxy-2-naphthyl)propionate phase at atmospheric pressure. This sodium racemate solution is desirably a 10–35 wt % solution, and if necessary, the concentration is adjusted to fall in this range by removal or addition of water. The aqueous sodium racemate phase is then washed with toluene to remove neutral impurities. Typically one to three toluene washes, preferably at least two, are used. A suitable temperature, typically 60–80° C., is maintained to prevent the racemic sodium 2-(6-methoxy-2-naphthyl)propionate from precipitating. The aqueous solution is then acidified with sulfuric acid in the presence of toluene at about 97° C. The aqueous phase is cut from the bottom of the reactor and the toluene solution of (±)-2-(6-methoxy-2-naphthyl) propionic acid is washed with water (typically twice) at about 95° C. to remove residual sulfuric acid. Racemic 2-(6-methoxy-2-naphthyl)propionic acid is then crystallized from the toluene solution.

Example 8 illustrates a preferred overall procedure for producing racemic 2-(6-methoxy-2-naphthyl)propionic acid on a large (1000 gallon) scale using recycle solvent (principally DEK and TEA) from a process conducted as in Example 7 above.

EXAMPLE 8

Vinylation Reaction

To a 1000 gallon reactor are charged 750 kg of BMN, a mixture of recycle solvent (DEK and TEA mixture containing typically about 1 wt % water) to give approximately 1305 kg of DEK and 368 kg of TEA. Catalyst consisting of 0.3 kg of $PdCl_2$, and 3.1 kg of NMDP is charged to the reactor. Fresh water is added (if necessary) to raise the water content of the reaction mixture to approximately 1.6 wt %. The reactor is then pressured to 100 psig with ethylene and the reactor temperature is adjusted to 95° C. The reactor is then pressured to 425–450 psig with ethylene and held at this pressure until the uptake of ethylene is completed. The reactor is cooled to 60° C. and excess ethylene is vented form the reactor. The reaction typically takes 4–6 hours to go to completion and typically gives a >95% BMN conversion and a MVN yield of 85–95%.

Workup and Hydrocarboxylation

Aqueous caustic (25% aqueous NaOH solution) is added to the reaction mixture containing MVN to liberate the TEA from the triethylamine hydrobromide salt. The aqueous layer is then separated from the organic layer, and the TEA is then recovered from the MVN, DEK, and TEA mixture by distillation. The distillate composed of DEK, TEA, and water is then recycled for use in the vinylation reaction. THF is added to the distillation residue (distilland or pot residue) composed mainly of a MVN/DEK mixture plus some solids to produce a MVN mixture containing THF and DEK in a weight ratio of about 1:1 suitable for carboxylation. The resultant mixture is filtered to remove the solids therefrom. Fresh catalyst and HCl are added in proportions corresponding to those of Example 7 and the hydrocarboxylation reaction is carried out as in Example 7. Then the (±)-2-(6-methoxy-2-naphthyl)propionic acid is converted to sodium (±)-2-(6-methoxy-2-naphthyl)propionate by the addition of 25 wt % aqueous sodium hydroxide solution, and the remainder of the racemic product workup and recovery procedure of Example 7 is carried out.

Examples 7 and 8 involve in part procedures (e.g., separation procedures) described in full in commonly-owned copending application Ser. No. 780,308, file Jan. 8, 1997, the entire disclosure of which is incorporated herein by reference.

Experimental work has shown that it is advantageous to carry out the separation of solids from the vinylation reaction product after the separation of the free amine and the replenishment of the solvent by addition of THF or like solvent (as in Examples 7 and 8), rather than before such separation and solvent addition. In particular, the filtration time is reduced significantly in this manner.

If in the vinylation reaction more than one solvent/diluent is used, the amine does not have to boil below all such solvent/diluents. Instead it should boil below at least one of the solvent/diluents that is makes up a substantial portion (e.g., at least 20 or 30%) of the total weight of such solvent/diluents. For example, a reaction conducted generally as in Example 7 above using a 1:1 (wt:wt) mixture of acetonitrile (ACN) and diethyl ketone (DEK) as the solvent/diluents, involves a situation in which the triethylamine boils above the ACN, but below the DEK. In such case, different workup procedures can be used. In one such procedure the ACN can be distilled (stripped) from the reaction mixture, and then the aqueous inorganic base solution is added followed by the phase separation and distillation of the triethylamine from the remaining organic phase. Another procedure involves adding the aqueous inorganic base solution, conducting the phase separation, and then distilling off the ACN and the triethylamine, leaving the diethyl ketone solution behind.

Example 9 illustrates a preferred procedure for producing BMN starting material for use in the practice of this invention.

EXAMPLE 9

Bromination of 2-Naphthol

2-Naphthol (144.8 g, 1.00 mol), EDC (537 g), and water (162 g) are charged to a 2-L reactor equipped with a reflux condenser, mechanical stirrer and peristaltic pump addition system. The reactor is heated to about 55° C. until most of the B-naphthol is dissolved. Bromine (336.9 g, 2.11 mol) is then added (sub-surface) via a pump at such a rate so as to maintain the reaction temperature at 60° C. After the bromine addition, the reaction temperature is maintained at 60° C. for 1.5 hour. The reaction is then cooled slightly and the lower phase (aq. HBr) siphoned off. The remaining EDC solution (841 g) is transferred out of the reactor and analyzed by GC. In a run conducted in this manner, the analysis showed 0.4% 2-naphthol, 92.6% 1,6-dibromo-2-naphthol (DBN), and 4.9% of other isomers.

Hydrodebromination of 1,6-Dibromo-2-Naphthol

A solution of DBN (271 g, 0.9 mol) in ethylene dichloride (EDC) (551 g), obtained from the bromination reaction, is charged in a 1000 Ml Hastalloy B autoclave. Tungsten carbide (82 g, 30 wt %) and tetrabutylammonium bromide (0.2 g, 0.1 wt %) are added and the reactor is sealed. The reactor is purged with hydrogen (50 psig) and vented three times and then pressured with hydrogen and heated to 90° C. A constant purge of hydrogen is maintained in such a rate that the pressure remains in the 120–125 psig range. Analysis of a reaction mixture produced after 5.5 hours in this manner showed 90% 6-bromo-2-naphthol, 2% DBN, and 2% 2-naphthol. The reactor is cooled to room temperature, vented to scrubbers, and the catalyst is permitted to settle. The EDC solution (747 g in a reaction conducted in this manner) is removed through the dip tube.

Methylation of 6-Bromo-2-Naphthol with MeCl

The EDC solution formed as above is transferred to a 1.4-liter (three pints) Chemco glass reactor with stainless steel head. It is first neutralized with dilute acid and then concentrated by distillation. Water (50 mL) is added to azeotropically remove traces of EDC left in the residue. Isopropyl alcohol (242 g) and sodium hydroxide (44 g, 1.1 mol; 88 g of 50% solution) are charged into the reactor. The reactor is sealed, purged with nitrogen, and heated to 70° C. Methyl chloride (MeCl) (66 g, 1.3 mol) is charged over a period of one hour (40–50 psig). After stirring at 80° C. for another hour, isopropyl alcohol is removed by distillation. The residue is heated to melted condition (90–95° C.) and then it is washed with water (400 g). Water is removed and the residue is distilled under vacuum (1 mm Hg). After removing small amounts of volatile materials, BMN is distilled at 160–165° C. as a white solid (169 g was formed in an operation conducted in this manner). Isopropyl alcohol (490 g) is added and the solution was heated to reflux and then slowly cooled down to about 10° C. Solid BMN is removed and washed with cold (0° C.) isopropyl alcohol (180 g) and then dried under vacuum at 70–75° C. Analysis of the white crystalline product formed in this manner showed 99.7 wt % BMN.

Example 9 involves procedures and subject matter described in full in commonly-owned copending application Ser. No. 780,309, filed Jan. 8, 1997, now U.S. Pat. No. 5,792,886, issued Aug. 11, 1998, the entire disclosure of which is incorporated herein by reference.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Without limiting the generality of the foregoing, as an illustrative example, where a claim specifies that a catalyst a palladium compound in combination with a tertiary phosphine ligand, this phraseology refers to the makeup of the individual substances before they are combined and/or mixed separately or concurrently with one or more other materials, and in addition, at the time the catalyst is actually performing its catalytic function it need not have its original makeup—instead whatever transformations, if any, that occur in situ as the catalytic reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for preparing an olefinic compound of the formula

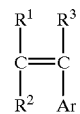

where Ar is aryl, substituted aryl, heteroaryl, substituted heteroaryl, benzyl, or substituted benzyl, and $R^1$, $R^2$, and $R^3$ are the same or different and are selected from hydrogen atoms, hydrocarbyl groups, functionally-substituted hydrocarbyl groups, and halogen atoms, which process comprises reacting at least one organic halide of the formula Ar—X, where Ar is as previously defined and X is a halogen atom of atomic number greater than 9, a diazonium group or a triflate group; with at least one olefinic compound of the formula

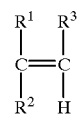

where $R^1$, $R^2$, and $R^3$ are as previously defined; in the presence of (A) a polar liquid reaction medium formed from (i) at least one liquid organic solvent/diluent, and (ii) a hydrogen halide acceptor consisting of at least one liquid secondary or tertiary amine;

(B) a catalytically effective amount of a catalyst system formed from (i) palladium or Pd(0) compound, and/or at least one salt of palladium in which the palladium has a valence of 1 or 2, and (ii) a tertiary phosphine ligand of the formula $R^4R^5R^6P$ where $R^4$, $R^5$, and $R^6$ are the same or different and are selected from alkyl, aryl, substituted aryl, heteroaryl, substituted heteroaryl, aralkyl, substituted aralkyl, cycloalkyl, and substituted cycloalkyl, at least one of $R^4$, $R^5$, and $R^6$ being aryl; and (C) an amount of water that accelerates the reaction, said amount of water being less than 5 percent of the total weight of the water plus said polar liquid reaction medium;

such that olefinic compound described above is formed without use of inorganic hydrogen halide acceptor.

2. A process according to claim 1 wherein Ar is unsubstituted or substituted aryl, and $R^1$, $R^2$, and $R^3$ are hydrogen atoms, $C_1$ to $C_6$ alkyl, substituted or unsubstituted phenyl, and/or trifluoromethyl.

3. A process according to claim 2 wherein Ar is phenyl substituted with alkyl, naphthyl substituted with alkoxy, phenyl substituted with aryloxy, aryl substituted with fluoro, or phenyl substituted with aroyl.

4. A process according to claim 3 wherein $R^1$, $R^2$, and $R^3$ are hydrogen atoms, methyl, and/or trifluoromethyl.

5. A process according to claim 4 wherein Ar is an isobutylphenyl group, and $R^1$, $R^2$, and $R^3$ are hydrogen atoms.

6. A process according to claim 4 wherein Ar is a methoxynaphthyl group, and $R^1$, $R^2$, and $R^3$ are hydrogen atoms.

7. A process according to claim 4 wherein Ar is a phenoxyphenyl group, and $R^1$, $R^2$, and $R^3$ are hydrogen atoms.

8. A process according to claim 4 wherein Ar is a fluorobiphenylyl group, and $R^1$, $R^2$, and $R^3$ are hydrogen atoms.

9. A process according to claim 4 wherein Ar is a benzoylphenyl group, and $R^1$, $R^2$, and $R^3$ are hydrogen atoms.

10. A process according to claim 2 wherein X is a bromine atom.

11. A process according to claim 3 wherein X is a bromine atom.

12. A process according to claim 2 wherein said tertiary phosphine ligand is neomenthyldiphenylphosphine.

13. A process according to claims 1 wherein the catalyst system is formed by introducing—(a) concurrently but separately, and/or (b) in admixture, and/or (c) separately in any sequence—into the reactor in which the reaction is to be carried out—whether the reactor is empty or contains one or more of said organic halide, said olefinic compound, said organic solvent/diluent, said hydrogen halide acceptor, and water—at least one salt of palladium and at least one cycloalkyldiphenyl phosphine, where the palladium of said salt has at least predominately, or if introduced into the reactor in admixture as in (b) initially had at least predominately, a valence of 2, whether or not it still has a valence of 2 at the time of introduction into said reactor.

14. A process according to claim 13 wherein said ligand is neomenthyldiphenylphosphine.

15. A process according to claim 3 wherein the catalyst system is formed by introducing—(a) concurrently but separately, and/or (b) in admixture, and/or (c) separately in any sequence—into the reactor in which the reaction is to be carried out—whether the reactor is empty or contains one or more of said organic halide, said olefinic compound, said organic solvent/diluent, said hydrogen halide acceptor, and water—at least one salt of palladium and at least one cycloalkyldiphenyl phosphine, where the palladium of said salt has at least predominately, or if introduced into the reactor in admixture as in (b) initially had at least predominately, a valence of 2, whether or not it still has a valence of 2 at the time of introduction into said reactor.

16. A process according to claim 1 wherein said polar liquid reaction medium consists essentially of a mixture formed from (i) at least one liquid ketone, and (ii) hydrogen halide acceptor consisting of at least one liquid tertiary amine in an amount of at least one equivalent per mole of said organic halide.

17. A process according to claim 1 wherein said polar liquid reaction medium comprises a mixture formed from (i) at least one liquid ketone, (ii) hydrogen halide acceptor consisting of at least one ketone-soluble tertiary monoamine in an amount of at least one mole per mole of said organic halide, and (iii) one or more additional liquid polar solvents selected from liquid nitrites and liquid N,N-dialkylalkanamides.

18. A process according to claim 17 wherein said polar liquid reaction medium consists essentially of a mixture formed from (i) at least one liquid dialkyl ketone, (ii) hydrogen halide acceptor consisting of at least one liquid trialkylamine, and (iii) at least one liquid nitrile of the formula RCN where R is an alkyl group.

19. A process according to claim 18 wherein said at least one liquid dialkyl ketone consists essentially of diethyl ketone, wherein said at least one liquid trialkylamine consists essentially of triethylamine, and wherein said at least one liquid nitrile consists essentially of acetonitrile.

20. A process according to claims 1 wherein said polar liquid reaction medium is a mixture formed from (i) at least one liquid dialkyl ketone and (ii) hydrogen halide acceptor consisting of at least one liquid trihydrocarbyl amine in an amount of at least one equivalent per mole of said organic halide; wherein said ketone has a boiling temperature higher than the boiling temperature of said amine; and wherein said medium is substantially devoid of any other polar liquid organic solvent.

21. A process according to claim 1 wherein said polar liquid reaction medium consists essentially of a mixture formed from (i) at least one liquid dialkyl ketone and (ii) hydrogen halide acceptor consisting of at least one liquid trialkylamine in an amount such that there are from about 1.05 to about 5.0 moles of said trialkylamine per mole of said organic halide.

22. A process according to claim 1 wherein said amount of water is in the range of about 1 to about 3.5 weight percent of the total weight of the water plus said polar liquid reaction medium.

23. A process for preparing an olefinic compound of the formula

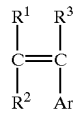

where Ar is a 6-alkoxy-2-naphthyl group, and $R^1$, $R^2$, and $R^3$ are the same or different and are selected from hydrogen atoms, hydrocarbyl groups, functionally-substituted hydrocarbyl groups, and halogen atoms, which process comprises reacting a 2-halo-6-alkoxynaphthalene in which the halogen atom is other than fluorine, with at least one olefinic compound of the formula

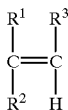

where $R^1$, $R^2$, and $R^3$ are as previously defined; in the presence of
- (A) a polar liquid reaction medium formed from (i) at least one liquid organic solvent/diluent, and (ii) a hydrogen halide acceptor consisting of at least one liquid secondary or tertiary amine;
- (B) a catalytically effective amount of a catalyst system formed from (i) palladium or Pd(0) compound, and/or at least one salt of palladium in which the palladium has a valence of 1 or 2, and (ii) a tertiary phosphine ligand of the formula

where $R^4$, $R^5$, and $R^6$ are the same or different and are selected from alkyl, aryl, substituted aryl, heteroaryl, substituted heteroaryl, aralkyl, substituted aralkyl, cycloalkyl, and substituted cycloalkyl, at least one of $R^4$, $R^5$, and $R^6$ being aryl; and
- (C) an amount of water that accelerates the reaction, and that is less than 5 weight percent of the total weight of the water plus said polar liquid reaction medium;

such that olefinic compound described above is formed without use of inorganic hydrogen halide acceptor.

24. A process according to claim 23 wherein the 2-halo-6-alkoxynaphthalene is a 2-bromo-6-alkoxynaphthalene; wherein said hydrogen halide acceptor is at least one liquid tertiary amine; wherein the catalyst system is formed by including in the reaction mixture before, during and/or after the formation of the rest of the initial reaction mixture catalytically effective amounts of (i) at least one salt of palladium in which the palladium has a valence of 1 or 2, and (ii) a tertiary phosphine ligand having two phenyl or alkyl-substituted phenyl groups and one cycloalkyl group.

25. A process according to claim 24 wherein the 2-bromo-6-alkoxynaphthalene is 2-bromo-6-methoxynaphthalene; wherein said at least one olefinic compound is ethylene; wherein said polar liquid reaction medium is formed from (i) at least one liquid organic solvent/diluent, and (ii) hydrogen halide acceptor consisting of triethylamine; wherein said at least one salt of palladium is a palladium(II) salt and wherein said a tertiary phosphine ligand is neomenthyldiphenylphosphine.

26. A process according to claim 25 wherein the liquid organic solvent/diluent consists essentially of at least one liquid ketone, wherein said palladium(II) salt is palladium (II) chloride or acetate; and wherein said amount of water is in the range of about 1 to about 3.5 weight percent of the total weight of the water plus said polar liquid reaction medium.

27. A process which comprises:
(1) reacting at least one organic halide of the formula Ar—X, where Ar is aryl, substituted aryl, heteroaryl, substituted heteroaryl, benzyl, or substituted benzyl, and X is a halogen atom of atomic number greater than 9, a diazonium group or a triflate group; with at least one olefinic compound of the formula

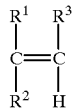

where $R^1$, $R^2$, and $R^3$ are the same or different and are selected from hydrogen atoms, hydrocarbyl groups, functionally-substituted hydrocarbyl groups, and halogen atoms; in the presence of
- (A) a polar liquid reaction medium formed from (i) at least one liquid organic solvent/diluent, and (ii) a hydrogen halide acceptor consisting of at least one liquid secondary or tertiary amine;
- (B) a catalytically effective amount of a catalyst system formed from (i) palladium or Pd(0) compound, and/or at least one salt of palladium in which the palladium has a valence of 1 or 2, and (ii) a tertiary phosphine ligand of the formula

where $R^4$, $R^5$, and $R^6$ are the same or different and are selected from alkyl, aryl, substituted aryl, heteroaryl, substituted heteroaryl, aralkyl, substituted aralkyl, cycloalkyl, and substituted cycloalkyl, at least one of $R^4$, $R^5$, and $R^6$ being aryl; and
- (C) an amount of water that accelerates the reaction, and that is less than 5 weight percent of the total weight of the water plus said polar liquid reaction medium;

to form without use of any inorganic hydrogen halide acceptor, a reaction product mixture containing a substituted olefin of the formula

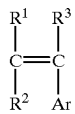

where Ar, $R^1$, $R^2$, and $R^3$ are as defined hereinabove; and
(2) catalytically carboxylating said substituted olefin with carbon monoxide in an liquid organic medium containing water or an alcohol and a catalytically effective amount of
- (A) a catalyst system formed from (i) palladium or at least one Pd(0) compound, and/or at least one salt of palladium in which the palladium has a valence of 1 or 2, and (ii) at least one tertiary phosphine ligand of the formula

where $R^4$, $R^5$, and $R^6$ are as defined hereinabove; or
- (B) a catalyst system formed from (i) palladium or at least one Pd(0) compound, and/or at least one salt of palladium in which the palladium has a valence of 1 or 2, (ii) at least one tertiary phosphine ligand of the formula

where $R^4$, $R^5$, and $R^6$ are as defined hereinabove, and (iii) at least one copper compound.

28. A process according to claim 27 wherein Ar is unsubstituted or substituted aryl, and $R^1$, $R^2$, and $R^3$ are hydrogen atoms, $C_1$ to $C_6$ alkyl, substituted or unsubstituted phenyl, and/or trifluoromethyl.

29. A process according to claim 27 wherein Ar is phenyl substituted with alkyl, naphthyl substituted with alkoxy, phenyl substituted with aryloxy, aryl substituted with fluoro, or phenyl substituted with aroyl.

30. A process according to claim 27 wherein $R^1$, $R^2$, and $R^3$ are hydrogen atoms, methyl, and/or trifluoromethyl.

31. A process according to claim 30 wherein Ar is an isobutylphenyl group, and $R^1$, $R^2$, and $R^3$ are hydrogen atoms.

32. A process according to claim 30 wherein Ar is a methoxynaphthyl group, and $R^1$, $R^2$, and $R^3$ are hydrogen atoms.

33. A process according to claim 30 wherein Ar is a phenoxyphenyl group, and $R^1$, $R^2$, and $R^3$ are hydrogen atoms.

34. A process according to claim 30 wherein Ar is a fluorobiphenylyl group, and $R^1$, $R^2$, and $R^3$ are hydrogen atoms.

35. A process according to claim 30 wherein Ar is a benzoylphenyl group, and $R^1$, $R^2$, and $R^3$ are hydrogen atoms.

36. A process according to claim 28 wherein X is a bromine atom.

37. A process according to claim 29 wherein X is a bromine atom.

38. A process according to claim 28 wherein said tertiary phosphine ligand is neomenthyldiphenylphosphine.

39. A process according to claim 27 wherein said liquid organic medium of (2) comprises at least a portion of the liquid organic solvent/diluent from (1) and at least one liquid ether, but is devoid or essentially devoid of amine; and wherein said medium contains water in an amount sufficient to result in hydrocarboxylation of said substituted olefin.

40. A process according to claim 27 wherein said polar liquid reaction medium of (1) consists essentially of at least one liquid ketone and at least one liquid tertiary amine; wherein said liquid organic medium of (2) comprises at least a portion of the ketone from (1) and at least one liquid ether, but is devoid or essentially devoid of amine; and wherein said medium contains water in an amount sufficient to result in hydrocarboxylation of said substituted olefin.

41. A process according to claim 27 wherein said organic halide is a 2-halo-6-alkoxynaphthalene in which the halogen atom is other than fluorine; wherein $R^1$, $R^2$, and $R^3$ are hydrogen atoms; wherein the amine of said polar liquid reaction medium of (1) is at least one liquid tertiary amine; wherein the catalyst system of (1) is formed by including in the reaction mixture before, during and/or after the formation of the rest of the initial reaction mixture catalytically effective amounts of (i) at least one salt of palladium in which the palladium has a valence of 1 or 2, and (ii) a tertiary phosphine ligand having two phenyl or alkyl-substituted phenyl groups and one cycloalkyl group; wherein said liquid organic medium of (2) comprises at least a portion of the liquid organic solvent/diluent from (1) and at least one liquid ether, but is devoid or essentially devoid of amine; and wherein said medium of (2) contains water in an amount sufficient to result in hydrocarboxylation of said substituted olefin.

42. A process according to claim 41 wherein the catalyst system of (2) is formed from (i) palladium or at least one Pd(0) compound, and/or at least one salt of palladium in which the palladium has a valence of 1 or 2, and (ii) at least one tertiary phosphine ligand of the formula $R^4R^5R^6P$ where $R^4$, $R^5$, and $R^6$ are as defined hereinabove.

43. A process according to claim 41 wherein the catalyst system of (2) is formed from (i) palladium or at least one Pd(0) compound, and/or at least one salt of palladium in which the palladium has a valence of 1 or 2, (ii) at least one tertiary phosphine ligand of the formula $R^4R^5R^6P$ where $R^4$, $R^5$, and $R^6$ are as defined hereinabove, and (iii) at least one copper compound.

44. A process according to claim 41 wherein the 2-halo-6-alkoxynaphthalene is 2-bromo-6-methoxynaphthalene; wherein the polar liquid reaction medium of (1) consists essentially of at least one liquid ketone and said at least one liquid tertiary amine; wherein the catalyst system of (2) is formed from (i) at least one salt of palladium in which the palladium has a valence of 1 or 2, and (ii) at least one tertiary phosphine ligand of the formula $R^4R^5R^6P$ where $R^4$, $R^5$, and $R^6$ are as defined hereinabove; such that said liquid organic medium of (2) comprises at least a portion of the ketone from (1) and at least one liquid ether, but is devoid or essentially devoid of amine, and contains water in an amount sufficient to result in hydrocarboxylation of said substituted olefin.

45. A process according to claim 44 wherein said liquid ketone is diethyl ketone; wherein said tertiary amine is triethylamine; wherein said amount of water in (1) is in the range of about 1 to about 3.5 weight percent of the total weight of the water plus said polar liquid reaction medium of (1); wherein the palladium salts used in the catalyst systems of (1) and of (2) are palladium(II) chloride or palladium(II) acetate; wherein the tertiary phosphine ligands used in the catalyst systems of (1) and of (2) are neomenthyldiphenylphosphine; and wherein the ether is tetrahydrofuran.

46. A process according to claim 41 wherein the 2-halo-6-alkoxynaphthalene is 2-bromo-6-methoxynaphthalene; wherein the polar liquid reaction medium of (1) consists essentially of at least one liquid ketone and said hydrogen halide acceptor; wherein said hydrogen halide acceptor consists of at least one liquid tertiary amine; wherein the catalyst system of (2) is formed from (i) at least one salt of palladium in which the palladium has a valence of 1 or 2, (ii) at least one tertiary phosphine ligand of the formula $R^4R^5R^6P$ where $R^4$, $R^5$, and $R^6$ are as defined hereinabove, and (iii) at least one copper compound; such that said liquid organic medium of (2) comprises at least a portion of the ketone from (1) and at least one liquid ether, but is devoid or essentially devoid of amine, and contains water in an amount sufficient to result in hydrocarboxylation of said substituted olefin.

47. A process according to claim 44 wherein said liquid ketone is diethyl ketone; wherein said tertiary amine is triethylamine; wherein said amount of water is in the range of about 1 to about 3.5 weight percent of the total weight of the water plus said polar liquid reaction medium of (1); wherein the palladium salts used in the catalyst systems of (1) and of (2) are palladium(II) chloride or palladium(II) acetate; wherein the tertiary phosphine ligands used in the catalyst systems of (1) and of (2) are neomenthyldiphenylphosphine; wherein the copper compound is a copper(II) halide other than fluoride; and wherein the ether is tetrahydrofuran.

48. A process according to claim 23 wherein said amount of water is in the range of about 1 to about 3.5 weight percent based on the weight of the water plus said polar liquid reaction medium.

49. A process according to claim 24 wherein said amount of water is in the range of about 1 to about 3.5 weight percent based on the weight of the water plus said polar liquid reaction medium.

50. A. A process according to claim 25 wherein said amount of water is in the range of about 1 to about 3.5 weight percent based on the weight of the water plus said polar liquid reaction medium.

51. A process according to claim 26 wherein said amount of water is in the range of about 1 to about 3.5 weight percent based on the weight of the water plus said polar liquid reaction medium.

52. A process for preparing 6-methoxy-2-vinylnaphthalene, which process comprises reacting 2-bromo-6-methoxynaphthalene with ethylene in the presence of (A) a polar liquid reaction medium formed from (i) a $C_4$–$C_8$ ketone, and (ii) a hydrogen halide acceptor consisting of a $C_4$–$C_9$ trialkyl amine;

(B) a catalytically effective amount of a catalyst system formed from (i) a palladium(II) salt and neomenthyldiphenylphosphine; and (C) a reaction accelerating amount of water; wherein the 2-bromo-6-methoxynaphthalene:Pd:neomenthyldiphenylphosphine mole ratio is in the range of about 1000–3000:1:2–10, respectively; wherein the mole ratio of amine:2-bromo-6-methoxynaphthalene is in the range of 1–2:1; wherein the mole ratio of ketone:amine is in the range of 1.0–4.0:1, respectively; and wherein the amount of water that accelerates the reaction is in the range of about 1 to about 3.5 weight percent of the total weight of the 2-bromo-6-methoxynaphthalene, the ketone, the trialkylamine, the palladium salt, the neomenthyldiphenylphosphine, and the water; such that 6-methoxy-2-vinylnaphthalene is formed without use of inorganic hydrogen halide acceptor.

53. A process according to claim 52, wherein the reaction temperature is in the range of about 60 to about 150° C., and the pressure of the ethylene used is in the range of about 400 to about 1000 psig.

54. A process according to claim 53 wherein the reaction temperature is in the range of about 80 to about 110° C.

55. A process for preparing 6-methoxy-2-vinylnaphthalene, which process comprises reacting 2-bromo-6-methoxynaphthalene with ethylene in the presence of (A) a liquid organic solvent/diluent consisting essentially of diethyl ketone or methyl isobutyl ketone;

(B) at least one liquid tertiary amine;

(C) a catalytically effective amount of a catalyst system formed from (i) a palladium(II) salt and neomenthyldiphenylphosphine; and (D) an amount of water that accelerates the reaction, said amount of water being insufficient to form a separate water layer in a mixture consisting of the amounts of (A), (B), and water being used, when a mixture of (A), (B), and water in the relative amounts being used is agitated for 10 minutes at 25° C. and allowed to stand for 15 minutes at the same temperature.

56. A process according to claim 55 wherein said amine is triethylamine.

* * * * *